US005801022A

United States Patent [19]
Navia et al.

[11] Patent Number: 5,801,022
[45] Date of Patent: *Sep. 1, 1998

[54] METHOD OF PRODUCING A PRODUCT WITH CROSSLINKED CRYSTALS OF THERMOLYSIN

[75] Inventors: Manuel A. Navia, Lexington; Nancy L. St. Clair, Charlestown, both of Mass.

[73] Assignee: Vertex Pharmaceuticals, Incorporated, Cambridge, Mass.

[*] Notice: The term of this patent shall not extend beyond the expiration date of Pat. No. 5,618,710.

[21] Appl. No.: 474,968

[22] Filed: Jun. 7, 1995

Related U.S. Application Data

[63] Continuation of Ser. No. 296,861, Aug. 26, 1994, abandoned, which is a continuation of Ser. No. 138,371, Oct. 15, 1993, abandoned, which is a continuation of Ser. No. 980,369, Nov. 23, 1992, abandoned, which is a continuation-in-part of Ser. No. 864,424, filed as PCT/US91/05415, Jul. 30, 1991, abandoned, which is a continuation-in-part of Ser. No. 720,237, Jun. 24, 1991, abandoned, which is a continuation-in-part of Ser. No. 562,280, Aug. 3, 1990, abandoned.

[51] Int. Cl.$^6$ .......................... C12P 13/22; C12P 13/20; G01N 33/543; C07K 17/00
[52] U.S. Cl. .................. 435/108; 424/94.1; 424/94.6; 424/94.63; 435/41; 435/109; 435/174; 435/195; 435/198; 435/212; 435/218; 436/518; 530/402; 530/413; 530/810
[58] Field of Search .......................... 435/174, 176, 435/180, 816, 41, 108, 109, 195, 198, 212, 218; 424/94.1, 94.6, 94.63; 436/518; 530/402, 413, 810

[56] References Cited

U.S. PATENT DOCUMENTS

| Re. 33,441 | 11/1990 | Wumpelmann et al. | 435/94 |
|---|---|---|---|
| 4,390,632 | 6/1983 | Carter | 436/10 |
| 4,411,996 | 10/1983 | Lloyd | 435/94 |
| 4,693,985 | 9/1987 | Degen et al. | 436/531 |
| 4,699,882 | 10/1987 | Visuri | 435/188 |
| 4,892,825 | 1/1990 | Wumpelmann et al. | 435/94 |
| 5,120,650 | 6/1992 | Visuri | 435/176 |
| 5,618,710 | 4/1997 | Navia et al. | 435/174 |

FOREIGN PATENT DOCUMENTS

| 0 092 829 | 11/1983 | European Pat. Off. |
|---|---|---|
| 0 166 427 | 1/1986 | European Pat. Off. |
| 0 169 767 | 1/1986 | European Pat. Off. |
| 0 175 582 | 3/1986 | European Pat. Off. |
| 0195311 | 9/1986 | European Pat. Off. |
| 0341503 | 11/1989 | European Pat. Off. |
| 0 367 302 | 5/1990 | European Pat. Off. |
| WO 85/03247 | 8/1985 | WIPO. |
| WO 86/00336 | 1/1986 | WIPO. |
| WO 91/05857 | 5/1991 | WIPO. |

OTHER PUBLICATIONS

Lee, et al., Bioorganic Chemistry 14, 202–210 (1986).
Nakanishi, et al., Bio/Technology, vol. 3, 1985, pp. 459–464.
Lindeberg, G., "A Convenient Synthesis of Aspartame," *Journal of Chemical Education*, 64:1062–1064 (1987).

Maugh, T.H., III, "A Renewed Interest in Immobilized Enzymes," *Science*, 223:474–476 (1984).

Quiocho, F.A. et al., "Intermolecular Cross Linking of a Protein . . . ," *Proceedings of the National Academy of Sciences USA*, 52:883–889 (1964).

Abstract J63017691, *World Patents Index Latest*, Derwent Publications Ltd., Jan. 1988.

Hupkes, J.V., "Practical Process Conditions for the Use of Immobilized Glucose Isomerase," *Starch*, 30:24–28 (1978).

Rehm, H.-J., "Aktuelle Probleme und Entwicklungen in der Biotechnologie," *Chem.-Ing.-Tech.*, 58:379–386 (1986).

Visuri, K. et al., "Enzymatic Production of High Fructose Corn Syrup (HFCS) Containing 55% Fructose in Aqueous Ethanol," *Biotech. & Bioeng.*, 30:917–920 (1987).

Barker, S.A. et al., "Enzymatic Processes for High–Fructose Corn Syrup," IN: *Enzymes and Immobilized Cells in Biotechnology*, Menlo Park, CA 1985.

(List continued on next page.)

*Primary Examiner*—David M. Naff
*Attorney, Agent, or Firm*—Fish & Neave; James F. Haley, Jr.; Margaret A. Pierri

[57] ABSTRACT

A protein such as an enzyme or antibody is immobilized by crosslinking crystals of the protein with a multifunctional crosslinking agent such as glutaraldehyde, and if desired lyophilizing the crosslinked crystals for storage. Crosslinking of the protein crystals provides stabilization for use under harsh conditions and for lyophilizing. The crystals crosslinked may be microcrystals having a cross-section of $10_{-1}$ mm or less. Crosslinked thermolysin, esterase, elastase, asparaginase and lysozyme crystals and crosslinked crystals of lipase from *Geotrichum candidum* and *Candida cylindracea* and of porcine origin can be used to convert a substrate to a product. Crosslinked thermolysin crystals are prepared that retain at least 96% of their initial activity after incubation for 4 days in the presence of a concentration of Pronase™ such as a thermolysin:Pronase™ ratio of 1:40 that causes the soluble uncrosslinked form of thermolysin that is crystallized to form the crystals that are crosslinked to lose at least 99% of its initial activity after incubation for 90 minutes under the same conditions. Crosslinked thermolysin crystals can be used to produce aspartame by combining the crystals with N-(benzyloxycarbonyl)-L-aspartic acid and L-phenylalanine methyl ester in a mixed aqueous/organic solvent such as a water-ethyl acetate mixture, and maintaining the combination under conditions to cause a condensation reaction to produce N-(benzyloxycarbonyl)-L-aspartyl-L-phenylalanine methyl ester, and removing the benzyloxycarbonyl group to obtain aspartame. Crosslinked antibody crystals have uses as an immunospecific reagent such as for detection of a substance in a sample, and for therapeutic purposes.

25 Claims, 10 Drawing Sheets

OTHER PUBLICATIONS

Visuri, K., "Industrial Scale Crystallization of Glucose Isomerase," Enzyme Engineering X International Conference, Sep. 24–29, 1989, Kashikojima, Japan.

Visuri, K. et al., "Purification and Characterisation of Crystalline B–Amylase from Barley," *Eur. J. Biochem.*, 28:555–565 (1972).

Visuri, K. et al., "A New Method for Protein Crystallization Using High Pressure," *Bio/Technology*, pp. 547–549, Jun. 1990.

Polvinen, K. et al., "Pilot–Scale Production and Properties of Lignin Peroxidases," In: *Enzymes in Biomass Conversion*, Amer. Chem. Soc., Boston, MA Apr. 22–27, 1990.

Visuri, K., "Crosslinked Crystalline Glucose Isomerase as Industrial Catalyst," Lecture in Detmold Starch Convention, 1992 (published after filing date of subject application).

Product Information SPEZYME$^R$ CIGI, Genencor International, publication date unknown.

Luenser, S., "Applications of Microbial Enzymes to Produce High Fructose Corn Syrup and Other Corn Sweeteners," publication date unknown.

Szabadalmi Kozlony es Vedjegyertesito, Budapest, 1990, Abstract T/52 817 (original in Hungarian, English translation).

G.M. Alter et al., "Kinetic Properties of Carboxypeptidase B in Solutions and Crystals", *Biochemistry*, 16, pp. 3663–3668 (1977).

G.J. Bartling et al., "Protein Modification in Nonaqueous Media—A New Method of Enzyme Cross–Linking", *Enzyme*, 18, pp. 310–316 (1974).

S.J. Bayne et al., "Enzymatically Active, Cross–Linked Pig Heart Lactate Dehydrogenase Crystals", *Carlsberg Res. Comm.*, 41, pp. 211–216 (1976).

W.H. Bishop et al., "Isoelectric Point of a Protein in the Crosslinked Crystalline State: β–Lactoglobulin", *J. Mol. Biol.*, 33, pp. 415–421 (1968).

A. Dyer et al., "A Thermal Investigation of the Stability of Crystalline Cross–Linked Carboxypeptidase A", *Thermochimica Acta*, 8, pp. 455–464 (1974).

D.J. Haas, "Preliminary Studies on the Denaturation of Cross–Linked Lysozyme Crystals", *Biophys. J.*, 8, pp. 549–555 (1968).

H.C. Hedrich et al., "Large–Scale Purification, Enzymic Characterization, and Crystallization of the Lipase from *Geotrichum Candidum*", *Enzyme & Microb. Technol.*, 13, pp. 840–847 (1991).

P.J. Kasvinsky et al., "Activity of Glycogen Phosphorylase in the Crystalline State", *J.Biol. Chem.*, 251, pp. 6852–6859 (1976).

H. Kirsten et al., "Catalytic Activity of Non–Cross–Linked Microcrystals of Aspartate Aminotransferase in Poly(ethylene glycol)", *Biochem. J.*, 211, pp. 427–434 (1983).

A.M. Klibanov, "Enzymatic Catalysis in Anhydrous Organic Solvents", *Trends in Biochem. Sci.*, 14, pp. 141–144 (1989).

D. Lombardo et al., "Crystallization and Preliminary X–ray Study of Horse Pancreatic Lipase", *J. Mol. Biol.*, 205, pp. 259–261 (1989).

T. Nakagawa et al., "Development of Effective Cross–Linking Method for Bioactive Substance–Enzyme Immobilization Using Glutaraldehyde Oligomers", *Chem. Pharm. Bull.*, 37, pp. 2463–2466 (1989).

F.A. Quiocho et al., "Effects of Changes in Some Solvent Parameters on Carboxypeptidase A in Solution and in Cross–Linked Crystals", *Proc. Nat. Acad. Sci.*, 57, pp. 525–537 (1967).

D.M. Shotton et al., "Conformational Changes and Inhibitor Binding at the Active Site of Elastase", *Cold Spring Harbour Symp. Quant. Bio.*, XXXVI, pp. 91–105 (1972).

C.A. Spilburg et al., "Kinetic Properties of Crystalline Enzymes. Carboxypeptidase A", *Biochemistry*, 16, pp. 1142–1150 (1977).

T. Tashima et al., "Structure of a New Oligomer of Glutaraldehyde Produced by Aldol Condensation Reaction", *J. Org. Chem.*, 56, pp. 694–697 (1991).

V.P. Torchlin et al., "The Principles of Enzyme Stabilization: III. The Effects of the Length of Intra–Molecular Cross–Linkages on the Thermostability of Enzymes", *Biochem. Biophys. Acta*, 522, pp. 277–283 (1978).

V.P. Torchlin et al., "Principles of Enzyme Stabilization: V. The Possibility of Enzyme Selfstabilization Under the Action of Potentially Reversible Intramolecular Cross–Linkages of Different Length", *Biochem. Biophys. Acta*, 568, pp. 1–10 (1979).

E. Tuchsen et al., "Kinetic Properties of Subtilisin Type Carlsberg in the Crystalline State", *Carlsberg Res. Comm.*, 42, pp. 407–420 (1977).

A. Yonath et al., "Crystallographic Studies of Protein Denaturation and Renaturation. 1. Effects of Denaturants on Volume and X–ray Pattern of Cross–Linked Triclinic Lysozyme Crystals", *Biochemistry*, 16, pp. 1413–1417 (1977).

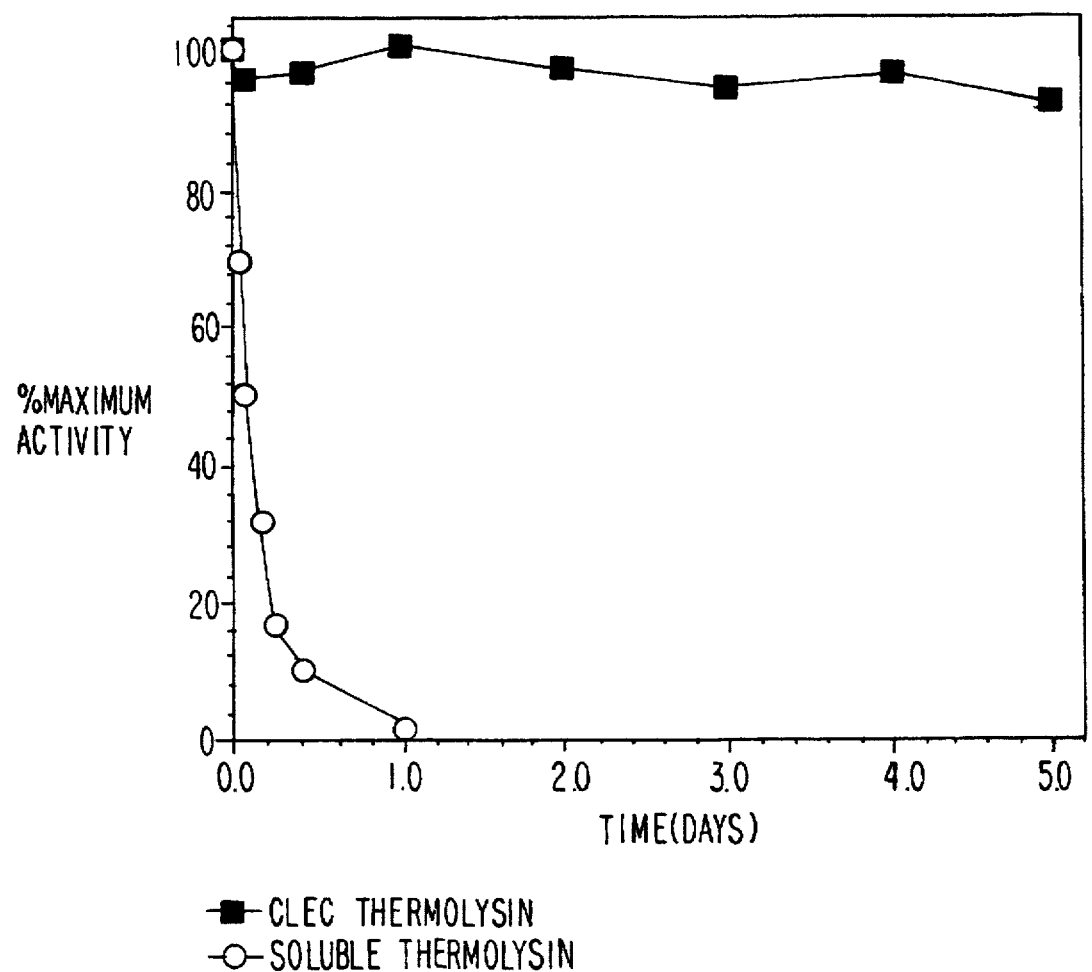

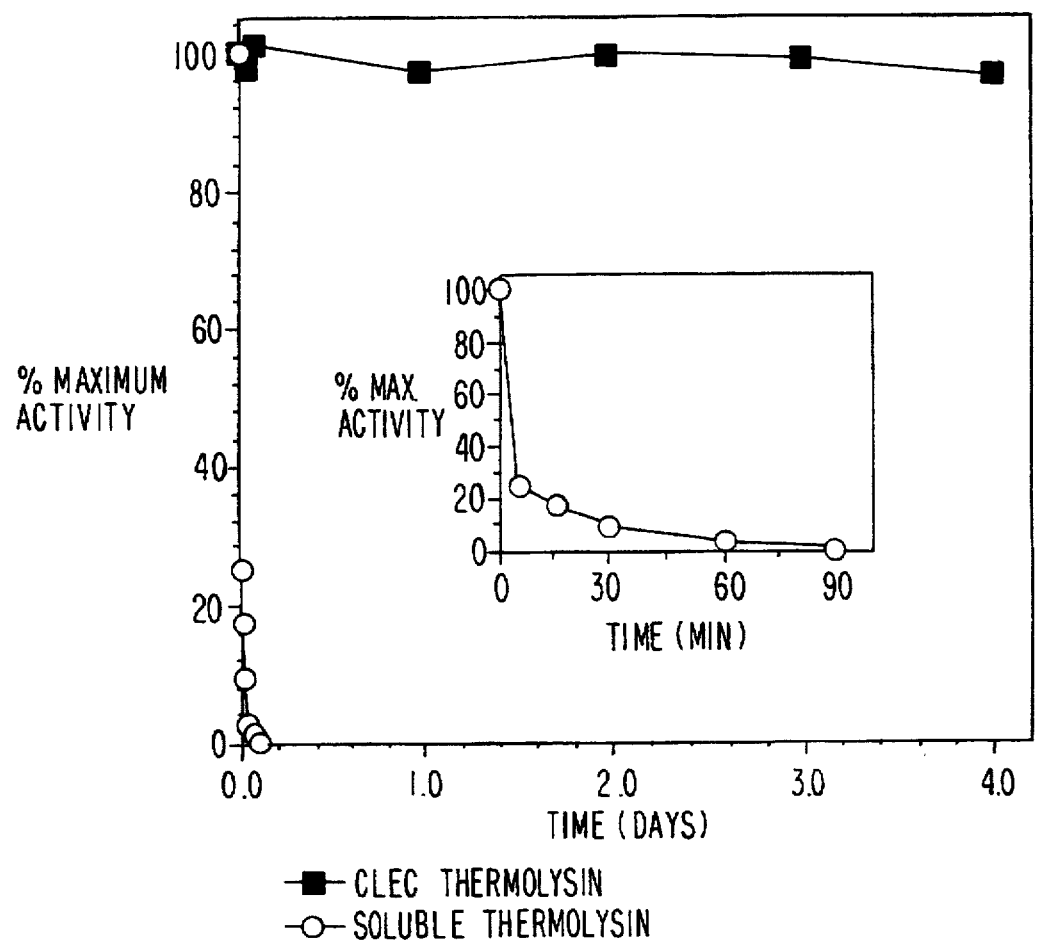

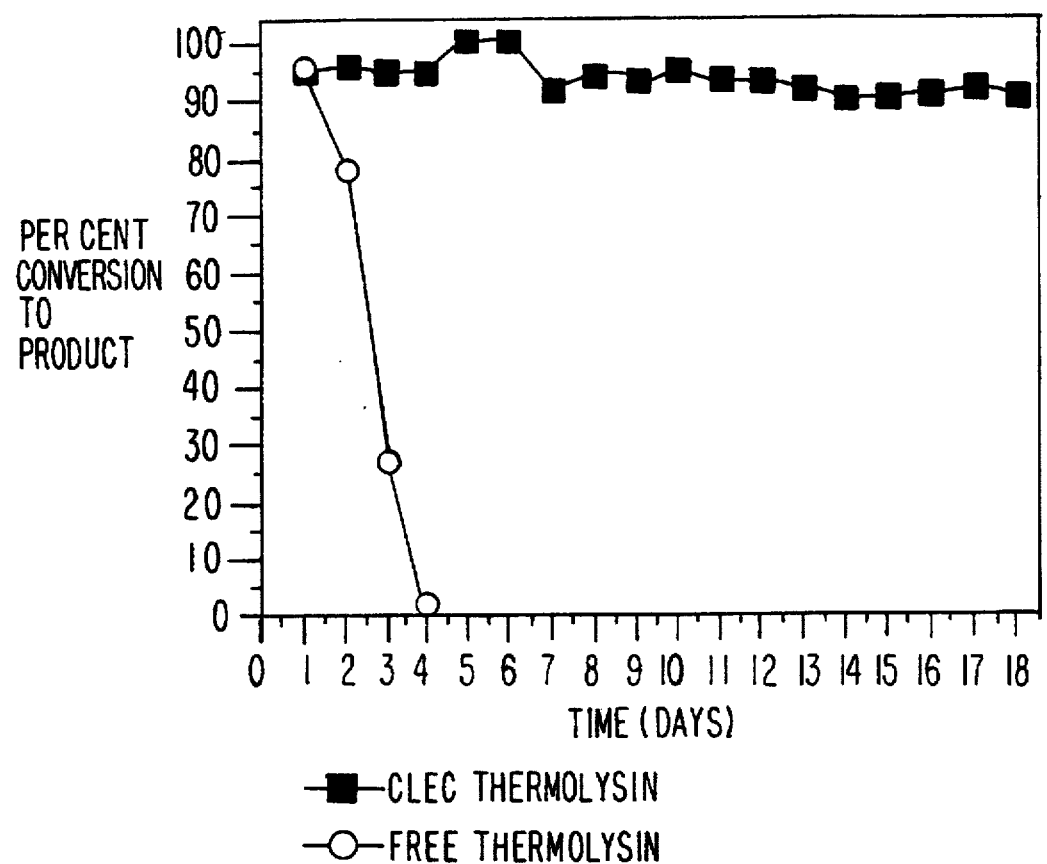

METHOD OF PRODUCING A PRODUCT WITH CROSSLINKED CRYSTALS OF THERMOLYSIN

RELATED APPLICATIONS

The application is a continuation of application Ser. No. 08/296,861, filed Aug. 26, 1994, which is a continuation of application Ser. No. 08/138,371, filed Oct. 15, 1993, which is a continuation of application Ser. No. 07/980,369, filed Nov. 23, 1992, which is a continuation-in-part of application Ser. No. 07/864,424, filed Apr. 6, 1992, which is a continuation-in-part of application Ser. No. 07/720,237, filed Jun. 24, 1991, which is a continuation-in-part of application Ser. No. 07/562,280, filed Aug. 3, 1990, all now abandoned. Priority is claimed to PCT application PCT/US91/05415, filed Jul. 30, 1991. The teachings of these applications are incorporated herein by reference.

BACKGROUND OF THE INVENTION

Enzymes are used as industrial catalysts for the large and laboratory scale economical production of fine and specialty chemicals (Jones, J. B., *Tetrahedron* 42: 3351–3403 (1986)), for the production of foodstuffs (Zaks et. al., *Trends in Biotechnology* 6: 272–275 (1988)), and as tools for the synthesis of organic compounds (Wong, C.-H., *Science* 244:1145–1152 (1989); *CHEMTRACTS-Org. Chem.* 3:91–111 (1990); Klibanov, A. M., *Acc. Chem. Res.* 23:114–120 (1990)).

Enzyme-based manufacturing can significantly reduce the environmental pollution burden implicit in the large scale manufacturing of otherwise unusable chemical intermediates, as shown in the large scale production of acrylamide using the enzyme, nitrile hydratase (Nagasawa, T. and Yamada, H., *Trends in Biotechnology* 7:153–158 (1989)).

Enzymes are also used in biosensor applications to detect various substances of clinical, industrial and other interest (Hall, E., "Biosensors", Open University Press (1990)). In the clinical area, enzymes may be used in extracorporeal therapy, such as hemodialysis and hemofiltration, where the enzymes selectively remove waste and toxic materials from blood (Klein, M. and Langer, R., *Trends in Biotechnology* 4:179–185 (1986)). Enzymes are used in these areas because they function efficiently as catalysts for a broad range of reaction types, at modest temperatures, and with substrate specificity and stereo-selectivity. Nonetheless, there are disadvantages associated with the use of soluble enzyme catalysts which have limited their use in industrial and laboratory chemical processes (Akiyama et al. *CHEMTECH* 627–634 (1988)).

Enzymes are expensive and relatively unstable compared to most industrial and laboratory catalysts, even when they are used in aqueous media where enzymes normally function. Many of the more economically interesting chemical reactions carried out in common practice are incompatible with aqueous media, where, for example, substrates and products are often insoluble or unstable, and where hydrolysis can compete significantly. In addition, the recovery of soluble enzyme catalyst from product and unreacted substrate in the feedstock often requires the application of complicated and expensive separation technology. Finally, enzymes are difficult to store in a manner that retains their activity and functional integrity, for commercially reasonable periods of time (months to years) without having to resort to refrigeration (4° C. to –80° C. to liquid $N_2$ temperatures), or to maintenance in aqueous solvents of suitable ionic strength, pH, etc.

Enzyme immobilization methods have, in many instances, circumvented these disadvantages. Immobilization can improve the stability of enzyme catalysts and protect their functional integrity in the harsh solvent environments and extreme temperatures characteristic of industrial and laboratory chemical processes (Hartmeier, W., *Trends in Biotechnology* 3:149–153 (1985)). Continuous flow processes may be operated with immobilized enzyme particles in columns, for example, where the soluble feedstock passes over the particles and is gradually converted into product. As used herein, the term enzyme immobilization refers to the insolubilization of enzyme catalyst by attachment to, encapsulation of, or by aggregation into macroscopic ($10^{-1}$ mm) particles.

A number of useful reviews of enzyme immobilization methods have appeared in the literature (Maugh, T. H., *Science* 223:474–476 (1984); Tramper, J., *Trends in Biotechnology* 3:45–50 (1985)). Maugh describes five general approaches to the immobilization of enzymes. These include: adsorption on solid supports (such as ion-exchange resins); covalent attachments to supports (such as ion-exchange resins, porous ceramics or glass beads); entrapment in polymeric gels; encapsulation; and the precipitation of soluble proteins by crosslinking them with bifunctional reagents in a random and undefined manner. In addition, one can immobilize whole cells (usually dead and made permeable) which have expressed the desired enzyme activity at high levels (e.g., Nagasawa, T. and Yamada, H., *Trends in Biotechnology* 7:153–158 (1989)).

Each of these immobilization procedures has its own advantages and limitations and none can be considered optimal or dominating. In most of them, the enzyme catalyst ultimately represents only a small fraction of the total volume of material present in the chemical reactor. As such, the bulk of the immobilized medium is made up of inert, but often costly carrier material. In all of them, the immobilizing interactions of the enzyme catalyst molecules with each other and/or with the carrier material tend to be random and undefined. As a result, although these interactions confer some enhanced stability to the enzyme catalyst molecules, their relative non-specificity and irregularity makes that stabilization sub-optimal and irregular. In most cases, access to the active site of the enzyme catalyst remains ill-defined. In addition, the immobilization methods described above fail to deal with problems associated with storage and refrigeration. Nor can conventionally immobilized enzymes generally be manipulated, as in being exchanged into one or another solvent of choice, without risk to the structural and functional integrity of the enzyme. In practical terms, except for the attached tether to the carrier particle, conventionally immobilized enzymes bear close resemblance to soluble enzymes, and share with them a susceptibility to denaturation and loss of function in harsh environments. In general, immobilization methods lead to a reduction of observed enzyme-catalyzed reaction rates relative to those obtained in solution. This is mostly a consequence of the limits of inward diffusion of substrate and outward diffusion of product within the immobilized enzyme particle (Quiocho, F. A., and Richards, F. M., *Biochemistry* 5:4062–4076 (1967)). The necessary presence of inert carrier in the immobilized enzyme particles increases the mean free path between the solvent exterior of the immobilized enzyme particle and the active site of the enzyme catalyst and thus exacerbates these diffusion problems. When dealing with immobilized cells, the diffusion problem is particularly severe, even if cell walls and membranes are made permeable to substrate and product in some way. One would further be concerned with the multitude of contaminating enzymatic activities, metabolites, and toxins contained in cells, and with the stability of cells in harsh solvents or extreme temperature operating environments. An improved immobilization technique which avoids the limitations of the presently available methods would be helpful in promoting the use of enzymes as industrial catalysts, particularly if it were shown to be useful on a large scale (Daniels, M. J., Methods in Enzymology 136: 371-379 (1987)).

SUMMARY OF THE INVENTION

The present invention relates to a method of immobilizing a protein, particularly an enzyme or an antibody, by forming crystals of the enzyme or antibody and, generally, also crosslinking the resulting crystals through use of a bifunctional reagent; crosslinked immobilized enzyme crystals (referred to as CLECs or CLIECs) made by this method; crosslinked immobilized antibody crystals (referred to as CLACS); the lyophilization of the resulting crystals as a means of improving the storage, handling, and manipulation properties of immobilized enzymes and antibodies; a method of making a desired product by means of a reaction catalyzed by a CLEC or a set of CLECs; and methods in which the CLACs of the present invention are used, such as a method of separating or purifying a substance or molecule of interest, in which a CLAC which recognizes (binds) the substance or molecule of interest serves as an immunospecific reagent. In another embodiment, a CLAC can be used for detection of a substance or molecule of interest in a sample, such as a biological sample, water, or other sample; this embodiment is useful, for example, for diagnostic purposes. In a further embodiment, CLACs of the present invention can be used for therapeutic purposes, in much the same manner monoclonal antibodies are now used therapeutically; in many instances, a CLAC of a particular enzyme can simply replace or substitute for presently-used (non-CLAC) antibodies. A particular advantage to CLACs is their enhanced resistance to degradation (e.g., enhanced protease resistance), relative to that of non-CLAC antibodies.

In the method of the present invention by which enzyme crystals are produced, small protein crystals (crystals of approximately $10^{-1}$ mm in size) are grown from aqueous solutions, or aqueous solutions containing organic solvents, in which the enzyme catalyst is structurally and functionally stable. In a preferred embodiment, crystals are then crosslinked with a bifunctional reagent, such as glutaraldehyde. This crosslinking results in the stabilization of the crystal lattice contacts between the individual enzyme catalyst molecules constituting the crystal. As a result of this added stabilization, the crosslinked immobilized enzyme crystals can function at elevated temperatures, extremes of pH and in harsh aqueous, organic, or near-anhydrous media, including mixtures of these. That is, a CLEC of the present invention can function in environments incompatible with the functional integrity of the corresponding uncrystallized, uncrosslinked, native enzyme or conventionally immobilized enzyme catalysts. CLACs can be made in a similar manner, using commercially available antibodies or antibodies produced against a specific antigen or hapten; entire antibodies or antibody fragments (e.g., FAb fragments) can be used to produce a corresponding CLAC.

In addition, CLECs made by this method can be subjected to lyophilization, producing a lyophilized CLEC which can be stored in this lyophilized form at non-refrigerated (room) temperatures for extended periods of time, and which can be easily reconstituted in aqueous, organic, or mixed aqueous-organic solvents of choice, without the formation of amorphous suspensions and with minimal risk of denaturation.

The present invention also relates to CLECs produced by the present method and to their use in laboratory and large scale industrial production of selected materials, such as chiral organic molecules, peptides, carbohydrates, lipids, or other chemical species. Presently, these are typically prepared by conventional chemical methods, which may require harsh conditions (e.g. aqueous, organic or near-anhydrous solvents, mixed aqueous/organic solvents or elevated temperatures) that are incompatible with the functional integrity of uncrystallized, uncrosslinked, native enzyme catalyst. Other macromolecules with catalytic activity can also be incorporated into the proposed CLEC technology. These might include catalytic antibodies (Lerner, R. A. et al., Science 252:659-667 (1991)) and catalytic polynucleotides (Cech, T. R., Cell 64:667-669 (1991); Celander, D. W., and Cech, T. R. Science 251:401-407 (1991)).

The present invention also relates to a method of making a selected product by means of a reaction catalyzed by a CLEC of the present invention.

In an example of the method and practice of the present invention, the enzyme thermolysin, a zinc metallo-protease, has been used to synthesize a chiral precursor of the dipeptidyl artificial sweetener, aspartame. The enzyme thermolysin was crystallized as described in Examples 1 and 2. The chiral aspartame precursor N-(benzyl-oxycarbonyl)-L-aspartyl-L-phenylalanine methyl ester (Z-Asp-Phe-OMeH-Phe-OMe, also referred to as Z-Asp-Phe-OMe-Phe-OMe) was synthesized in a condensation reaction catalyzed by the thermolysin CLEC, in which the two substrates acted upon were N-(benzyloxycarbonyl)-L-aspartic acid (Z-L-Asp, also referred to as CBz-L-Asp) and L-phenylalanine methyl ester (L-Phe-OMe). As described herein, thermolysin CLECs of the present invention have been shown to exhibit great stability even under harsh conditions and for an extended period (24 hour cycles, over a period of 18 days, in buffer-saturated ethyl acetate at 55° C). This was evidenced by the fact that at the end of 18 days, the thermolysin CLECs exhibited substantially the same enzymatic activity as they had on day one. In comparison, free thermolysin was inactivated, under the conditions used, after four days.

In another example of the method and practice of the present invention, and as disclosed here, the enzyme lipase from three sources (Geotrichum (G.) candidum, Candida cylindracea and porcine pancreas) was crystallized and crosslinked, as described in the examples. In addition, the G. candidum lipase CLEC was lyophilized, as described in Example 2. Examples 5-8 describe lipase CLECs.

BRIEF DESCRIPTION OF THE DRAWINGS

FIG. 3 is a graphic representation of measurement of the activity of soluble and crystalline thermolysin after incubation at 65° C.

FIG. 4 is a graphic representation of results of assessment of resistance of soluble and thermolysin CLEC to exogenous proteolytic degradation.

FIG. 6 is a graphic representation of the activity of thermolysin CLECs and of free thermolysin at 55° C. over a period of 18 days, in buffer-saturated ethyl acetate.

DETAILED DESCRIPTION OF THE INVENTION

Figure 1:
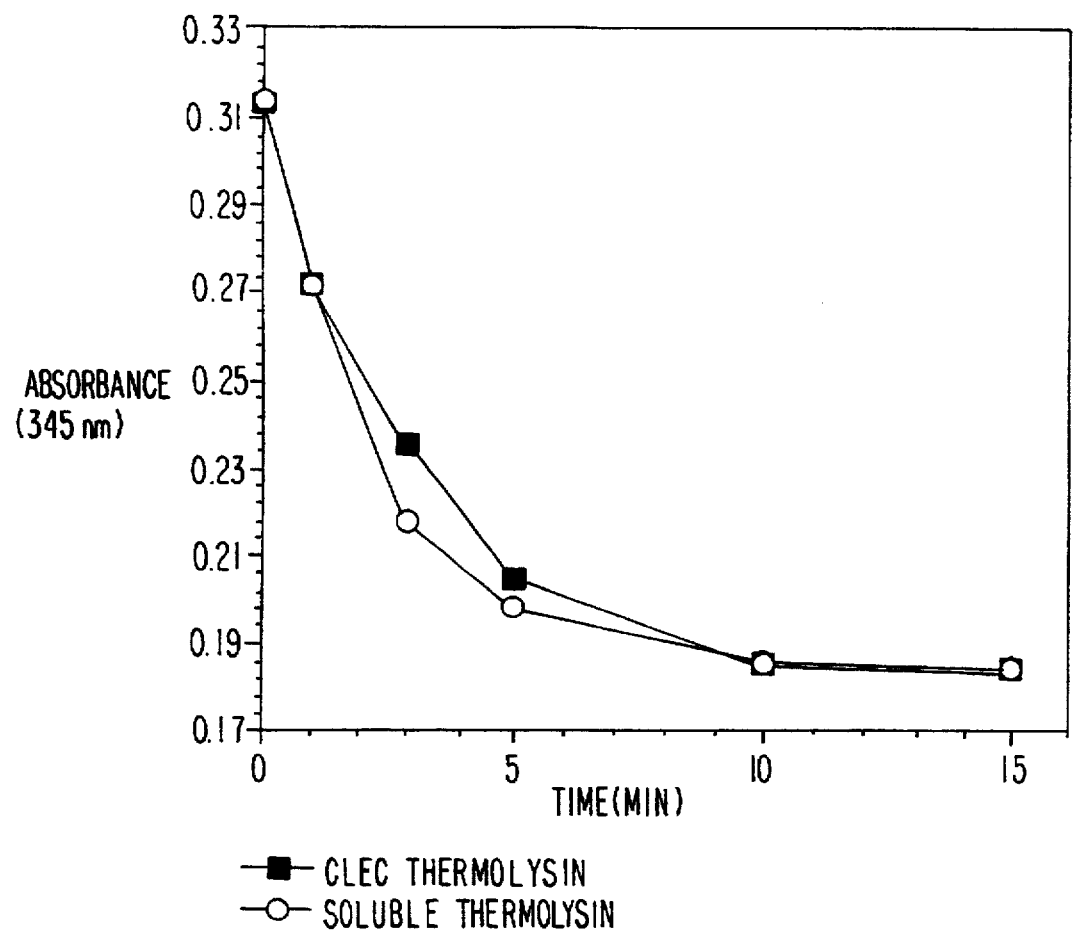
FIG. 1 is a graphic representation of results of assessment of enzymatic activity of soluble and thermolysin CLEC.

A simple, general procedure that assures stability and function for a given enzyme or set of enzymes under conditions which are of interest to the synthetic chemist and which are too harsh for use with enzymes using presently available methods, would be very useful. Cross-linked immobilized enzyme crystals (referred to as CLECs or CLIECs) as described here have been shown to be useful. Stabilization of the crystal lattice and of the constituent enzyme catalysts in the crystal by the cross-linking reaction permits the use of CLECs in environments, including aqueous, organic or near-anhydrous solvents, mixtures of these solvents, extremes of pH and elevated temperatures, which are incompatible with enzyme function using presently available methods. In addition, the stabilization of the crystal lattice in CLECs makes possible the lyophilization of CLECs by standard methods. Lyophilized CLECs can be stored for commercially attractive periods of time (months to years) in the absence of refrigeration, and facilitate the rapid and uncomplicated utilization of CLECs in industrial and laboratory scale processes by the simple addition of solvents of choice, without need for intervening solvent exchange processes. CLECs are also highly resistant to digestion by exogenous proteases. The method of the present invention facilitates the use of versatile enzyme catalysts in mainstream industrial chemical processes, as well as in the laboratory synthesis of novel compounds for research.

Although crosslinking contributes to the stability of a crystal enzyme, it is neither necessary nor desirable in all cases. Some crystallized enzymes retain functional and structural integrity in harsh environments even in the absence of crosslinking. The preferred embodiment of the present method includes cross-linking of a crystal enzyme and is described in detail in the following sections and in commonly owned, U. S. patent application Ser. Nos. 07/864, 424, 07/720,237, 07/562,280 and PCT/US91/05415, the teachings of which are expressly incorporated herein. It is to be understood, however, that crystallized enzymes which are not subsequently cross-linked can be used in some embodiments of the present invention.

The regular interactions between the constituent enzyme molecules in the crystal lattice of a CLEC result in well defined pores of limited size leading to the enzyme molecules within the body of a CLEC. As a result, substrates larger than the available pore size will not penetrate the body of the CLEC particle.

As a consequence of the limited pore size, many enzymatic reactions of commercial and academic interest involving substrates larger than the pore size of the CLECs would be beyond the scope of the present invention. This would include most reactions involving large polymers, such as proteins, polynucleotides, polysaccharides, and other organic polymers, where the number of polymeric subunits would be such as to male the polymer larger than the crystal pore size in CLECs. In such instances, however, catalysis can still take place on the CLEC surface.

The present invention is a method of immobilizing a selected protein, particularly an enzyme, by crystallizing and crosslinking the protein, resulting in production of a crosslinked immobilized enzyme crystal (CLEC) which can be used to catalyze production of a selected product, such as a peptide, carbohydrate, lipid or chiral organic molecule. The selected product can be produced by altering a single substrate (e.g., to produce a breakdown product or other product) or by combining the substrate with an additional substance or substances (e.g., a second substrate, molecule or compound to be added through the action of the CLEC). The present invention further relates to such CLECs and to a method of making a selected product by means of a CLEC-catalyzed reaction or CLEC-catalyzed step in a series of reactions. In one embodiment of the present invention, the dipeptidyl precursor of aspartame has been produced in a condensation reaction catalyzed by cross-linked immobilized thermolysin made by the present method. In another embodiment of this invention, the indicator substrate, FAGLA, has been cleaved to produce a calorimetric product, whose presence is indicative of enzyme activity in a thermolysin CLEC. FAGLA hydrolysis has been used as a model reaction to indicate the robustness of the thermolysin CLEC in a number of environments that would be normally incompatible with that enzyme's activity.

In other embodiments of this invention, described in greater detail and claimed in the earlier-referenced commonly-owned patent applications, the enzymes elastase, esterase, lipase, asparaginase, and lysozyme have been used to cleave various indicated substances, such as p-nitrophenyl acetate (esterase and lipase), succinyl-(ala)3-p-nitroanilide (elastase), 4-methylumbelliferyl N-acetyl-chitrioside (lysozyme) and NADH (asparaginase) and urea (urease). In particular herein, crystallization, crosslinking and lyophilization of lipase, from Candida and of porcine origin, are also described and claimed.

By the method of this invention, one of ordinary skill in the art can adapt a protocol for making a desired product by means of a reaction catalyzed by an immobilized enzyme. The enzyme of interest, when crystallized from an appropriate solution, can be cross-linked with glutaraldehyde or other suitable bifunctional reagent in the crystallization solution to produce a CLEC of that enzyme. Subsequently, the CLEC of the enzyme of choice can be lyophilized as described in Example 2.

There are several advantages which the use of a CLEC offers over presently-available enzyme-catalyzed methods. For example, the cross-linked crystal matrix in a CLEC provides its own support. Expensive carrier beads, glasses, gels, or films are not required in order to tie down the enzyme catalyst, as they are in presently-available immobilization methods. As a result, the concentration of enzyme in a CLEC is close to the theoretical packing limit that can be achieved for molecules of a given size, greatly exceeding densities achievable even in concentrated solutions. The entire CLEC consists of active enzyme (and not inactive carrier), and thus, the diffusion-related reduction of enzyme reaction rates usually observed with conventionally immobilized enzymes relative to enzymes in solution should be minimized, since the mean free path for substrate and product between active enzyme and free solvent will be greatly shortened for CLECs (compared to a conventional immobilized enzyme carrier particles). These high protein densities will be particularly useful in biosensor, analytical and other applications requiring large amounts of protein in small volumes. In industrial processes, the superior performance and compactness of CLECs results in significant operating economies, by increasing the effective activity of a given volume of catalyst, thereby allowing reductions in plant size, as well as capital costs (Daniels, M. J., *Methods in Enzymol.* 136:371–379 (1987)). CLECs are relatively monodispersed, with a macroscopic size and shape reflecting natural crystal growth characteristics of the individual enzyme catalysts. Replacement of existing carrier-immobilized enzyme media with CLECs should not be difficult, since both systems are comparable in size and shape, and both can be similarly recovered from feedstock by any number of simple methods, including basic economical operations such as filtration, centrifugation, decantation of solvent, and others.

In addition, the use of lyophilized CLECs permits routine handling and storage of these materials prior to use (dry storage at room temperature without refrigeration, for extended periods of time). Lyophilized CLECs also allow for routine formulation by direct addition of solvents and substrates of interest, without lengthy solvent exchange processes, or the formation of amorphous suspensions. The lyophilized CLEC form extends the general utility of the enzymes as catalysts to a broader spectrum of enzymes and functional conditions.

A second advantage of a CLEC is that cross-linking of the crystallized enzyme stabilizes and strengthens the crystal lattice and the constituent enzyme molecules, both mechanically and chemically. As a result, a CLEC may be the only means of achieving significant concentrations of active enzyme catalyst in harsh aqueous, organic, near-anhydrous solvents, or in aqueous-organic solvent mixtures. The use of enzymes as catalysts in organic syntheses has been hampered by their tendency to denature in the presence of non-aqueous solvents, and particularly, in mixtures of aqueous and non-aqueous solvents (Klibanov, A. M., *Trends in Biochemical Sciences*, 14:141–144 (1989)). In CLECs, the restriction of conformational mobility that leads to stability is provided by the inter- molecular contacts and cross-links between the constituent enzyme molecules making up the crystal lattice, rather than by the near-absence of water in the medium. As a result, intermediate water concentrations can be tolerated by enzymes when formulated as CLECs, as has previously not been possible (see Table 7). In commercial applications, aqueous-organic solvent mixtures allow manipulation of product formation by taking advantage of relative solubilities of products and substrates. Even in aqueous media, enzyme catalysts, immobilized or soluble, are subject to mechanical forces within a chemical reactor that can lead to denaturation and a shortened half-life. The chemical cross-links within the CLEC provide the necessary mechanical strength (Quiocho and Richards, *Proc. Natl. Acad. Sci.* (*USA*) 52:833–839 (1964)) that results in increased reactor life for the enzyme catalyst.

A third advantage of a CLEC is that as a result of its crystalline nature, a CLEC can achieve uniformity across the entire cross-linked crystal volume. Crystalline enzymes as described herein are grown and crosslinked in an aqueous environment and, therefore, the arrangement of molecules within the crystal lattice remains uniform and regular. This uniformity is maintained by the inter-molecular contacts and chemical cross-links between the enzyme molecules constituting the crystal lattice, even when exchanged into other aqueous, organic or near-anhydrous media, or mixed aqueous/organic solvents. In all of these solvents, the enzyme molecules maintain a uniform distance from each other, forming well-defined stable pores within the CLECs that facilitate access of substrate to the enzyme catalysts, as well as removal of product. Uniformity of enzyme activity is critical in industrial, medical and analytical applications where reproducibility and consistency are paramount.

A fourth advantage of using a CLEC is that it should exhibit an increased operational and storage half-life. Lattice interactions, even in the absence of cross-linking, are known to stabilize proteins, due in part to restrictions of the conformational degrees of freedom needed for protein denaturation. In CLECS, the lattice interactions, when fixed by chemical cross-links, are particularly important in preventing denaturation, especially in mixtures of aqueous and non-aqueous solvents (Klibanov, A. M., *Trends in Biochemical Sciences* 14:141–144 (1989)). Enzymes that have been in the crystalline state for months or years routinely retain a high percentage of their catalytic activity. Cross-linked immobilized enzyme crystals stored in anhydrous solvents will be even further protected from microbial contamination and damage, which is a serious problem in storing large quantities of protein in a nutrient rich, aqueous environment. In the case of a lyophilized CLEC, the immobilized enzyme is stored in the absence of solvent. That, and the stabilization achieved by cross-linking allows for the storage in the absence of refrigeration for long periods of time.

A fifth advantage of using a CLEC is that it should exhibit enhanced temperature stability as a consequence of the cross-links stabilizing the crystal lattice. Carrying out reactions at a higher temperature than that used with conventional methods would increase reaction rates for the chemical reactions of interest, both thermodynamically, and by enhancing the diffusion rate into and out of the crystal lattice of CLECs. These combined effects would represent a major improvement in reaction efficiency, because they would maximize the productivity of a given quantity of enzyme catalyst, which is generally the most expensive component of the reaction process (Daniels, M. J., *Methods in Enzymol.* 136:371–379 (1987)). The temperature stability exhibited by CLECs is remarkable because most enzyme systems require mild reaction conditions. CLECs would also be stabilized against denaturation by transient high temperatures during storage.

A final advantage of use of a CLEC is that pores of regular size and shape are created between individual enzyme molecules in the underlying crystal lattice. This restricted solvent accessibility greatly enhances the metal ion or cofactor retention characteristics of CLECs as compared to conventionally immobilized enzymes and enzymes in solution. This property of CLECs will permit the use of economically superior continuous-flow processes in situations (see e.g. Oyama et al. *Methods in Enzymol.* 136: 503–516 (1987)) where enzyme would otherwise be inactivated by metal ion or cofactor leaching. For example, in the thermolysin-mediated synthesis of the dipeptidyl aspartame precursor, Z-L-Asp-L-Phe-OMe, conventionally immobilized enzyme is known to lose catalytic activity in continuous-flow column processes, in part through the leaching of calcium ions essential for thermolysin activity. In practice, leaching of calcium ions has forced the use of less efficient batch processes (Nakanishi et al., *Biotechnology* 3:459–464 (1985)). Leaching occurs when calcium ion complexes are formed with substrate Z-L-Asp, in competition with the natural calcium binding sites on the surface of the enzyme, resulting in the loss of catalytic activity. The high density of enzyme, and the correspondingly limited volume accessible to solvent in the interstices of the CLECs, discourages the formation of the competing L-Asp-$Ca^{++}$ complexes responsible for metal ion leaching.

In addition, crystallized, crosslinked antibodies, or CLACs, made by a method similar to that used to produce CLECs, are the subject of the present invention. As described with reference to CLECs, although crosslinking contributes to the stability of a crystallized antibody, it is neither necessary nor desirable in all instances. Crystallized antibodies which are not subsequently cross-linked can be used in some embodiments of the present invention. CLACs of the present invention have the same advantages as described herein for CLECs. A particularly useful advantage is the enhanced resistance to degradation (e.g., protease degradation) of CLACs.

Preparation of CLECs—enzyme crystallization

In the method of the present invention, a crosslinked immobilized enzyme crystal (or CLEC) is prepared as follows: Enzyme crystals are grown by the controlled precipitation of protein out of aqueous solution, or aqueous solution containing organic solvents. Conditions to be controlled include, for example, the rate of evaporation of solvent, the presence of appropriate co-solutes and buffers, and the pH and temperature. A comprehensive review of the various factors affecting the crystallization of proteins has been published by McPherson (*Methods Enzymol.* 114:112 (1985)). In addition, both McPherson and Gilliland (*J. Crystal Growth* 90:51–59 (1988)) have compiled comprehensive lists of all proteins and nucleic acids that have been reported as crystallized, as well as the conditions that lead to their crystallization. A compendium of crystals and crystallization recipes, as well as a repository of coordinates of solved protein and nucleic acid crystal structures, is maintained by the Protein Data Bank (Bernstein et al. *J. Mol. Biol.* 112:535–542 (1977)) at the Brookhaven National Laboratory. Such references can be used to determine the conditions necessary for the crystallization of a given protein or enzyme previously crystallized, as a prelude to the formation of an appropriate CLEC, and can guide the formulation of a crystallization strategy for proteins that have not. Alternatively, an intelligent trial and error search strategy (see eg., Carter, C. W. Jr. and Carter, C. W., *J. Biol. Chem.* 254:12219–12223 (1979)) can, in most instances, produce suitable crystallization conditions for most proteins, including, but not limited to, those discussed above, provided that an acceptable level of purity can been achieved for these. The level of purity required can vary widely from protein to protein. In the case of lysozyme, for example, the enzyme has been crystallized directly from its unpurified source, the hen egg-white (Gilliland, G. L., *J. Crystal Growth* 90:51–59 (1988)). For use as CLECs in the method of this invention, the large single crystals which are needed for X-ray diffraction analysis are not required, and may, in fact, be undesirable because of diffusion problems related to crystal size. Microcrystalline showers (i.e., crystals in the order of $10^{-1}$ mm in size/cross section) are suitable for CLECs and are often observed, although seldom reported in the X-ray crystallographic literature. Micro-crystals are very useful in the method of this invention to minimize problems with diffusion (see eg., Quiocho, F. A., and Richards, F. M., *Biochemistry* 5:4062–4076 (1967)).

In general, crystals are produced by combining the protein to be crystallized with an appropriate aqueous solvent or aqueous solvent containing appropriate precipitating agents, such as salts or organics. The solvent is combined with the protein at a temperature determined experimentally to be appropriate for the induction of crystallization and acceptable for the maintenance of protein stability and activity. The solvent can optionally include co-solutes, such as divalent cations, cofactors or chaotropes, as well as buffer species to control pH. The need for co-solutes and their concentrations are determined experimentally to facilitate crystallization. In an industrial scale process, the controlled precipitation leading to crystallization can best be carried out by the simple combination of protein, precipitant, cosolutes, and optionally buffers in a batch process. Alternative laboratory crystallization methods, such as dialysis, or vapor diffusion can also be adapted. McPherson (*Methods Enzymol.* 114:112 (1985)), and Gilliland (*J. Crystal Growth* 90:51–59 (1988)) include a comprehensive list of suitable conditions in their reviews of the crystallization literature. Occasionally, incompatibility between the cross-linking reagent and the crystallization medium might require exchanging the crystals into a more suitable solvent system.

Many of the proteins for which crystallization conditions have already been described in the literature, have considerable potential as practical enzyme catalysts in industrial and laboratory chemical processes, and are directly subject to formulation as CLECs within the method of this invention. These are described in the referenced commonly-owned patent applications.

Preparation of CLECs—cross-linking reaction

Once crystals are grown in a suitable medium, they can be cross-linked. Cross-linking results in stabilization of the crystal lattice by introducing covalent links between the constituent enzyme molecules in the crystal. This makes possible the transfer of enzyme into an alternate-reaction environment that might otherwise be incompatible with the existence of the crystal lattice, or even with the existence of intact undenatured protein. Cross-linking can be achieved by a wide variety of bifunctional reagents, although in practice, simple, inexpensive glutaraldehyde has become the reagent of choice. (For a representative listing of other available cross-linking reagents, one can consult, for example, the 1990 catalog of the Pierce Chemical Company). Cross-linking with glutaraldehyde forms strong covalent bonds between primarily lysine amino acid residues within and between the enzyme molecules in the crystal lattice that constitute the crystal. The cross-linking interactions prevent the constituent enzyme molecules in the crystal from going back into solution, effectively insolubilizing or immobilizing the enzyme molecules into microcrystalline (ideally $10^{-1}$ mm) particles. The macroscopic, immobilized, insolubilized crystals can then be readily separated from the feedstock containing product and unreacted substrate by simple procedures such as filtration, decantation, and others. They can also be used in CLEC packed columns in continuous flow processes, where they exhibit enhanced cofactor and metal ion retention properties.

By the method of this invention, CLECs are obtained for use as enzyme catalysts in existing and novel environments. The enhanced stability of the CLECs, which results from the cross-linking reaction, makes it possible to transfer the CLEC into a solvent (e.g., aqueous, organic or near-anhydrous solvents, or a mixture of these), in which it would otherwise be incompatible, and to carry out chemical reactor operation at elevated temperatures of extremes of pH. The macroscopic CLEC catalyst particles can also be readily manipulated, allowing recovery from feedstock by simple methods, such as filtration, centrifugation, or decantation of solvent. In addition, these can be used in packed columns in continuous flow processes.

Preparation of CLECs—lyophilization

A suspension of one volume of cross-linked thermolysin crystals in ten volumes of demineralized water at pH 7.0 was lyophilized overnight using a VirTis Model #24 lyophilizer. Lyophilized crystals were stored at room temperature or at 4° C. prior to reconstitution, which was accomplished by adding ten volumes of the solvent of choice directly onto crystals taken from storage. Rehydrated crystals were reconstituted in 10 mM calcium acetate buffer at pH 7.0 for the FAGLA cleavage experiments. Reconstituted lyophilized CLECs were routinely stored at room temperature. In contrast, soluble enzyme required storage at −70° C. to maintain specific activity longer than a week. This protocol was used for all the enzymes described in the exemplification included here.

Synthesis of aspartame precursor with thermolysin CLEC

The method of the present invention, by which cross-linked crystal enzymes are produced, is described below and exemplified by the production of cross-linked immobilized enzyme crystals of thermolysin for use in the production of the dipeptidyl precursor of aspartame, in ethyl acetate, which is a near-anhydrous organic solvent. Thermolysin, a protein which has been crystallized and whose structure has been solved at 1.6 Å resolution (Holmes and Matthews, *J. Mol. Biol.* 160:623–639 (1982)), is one example of an enzyme which can be used as a CLEC in the present method. Thermolysin is used in the manufacture of the artificial sweetener aspartame (Isowa et al. U.S. Pat. No. 4,436,925 (1984); Lindeberg, *J. Chem. Ed.* 64: 1062–1064 (1987); Nakanishi et al., *Biotechnology* 3: 459–464 (1985); Oyama, et al., *Methods in Enzymol.* 136: 503–516 (1987)). At the present time, most aspartame appears to be produced by a conventional synthetic chemistry approach, although use of conventionally immobilized thermolysin in near-anhydrous media has produced encouraging results (Oyama et al., *J. Org. Chem.* 46:5242–5244 (1981); Nakanishi et al., *Biotechnology* 3:459–464 (1985)). Improvement in the enzymatic approach to aspartame production, such as is possible through use of the present method, would make it competitive with the presently-used method, both in terms of convenience and cost (Oyama, et al., *Methods in Enzymol.* 136:503–516 (1987)).

Assessment of thermolysin CLECs

The method of the present invention has also been used to produce thermolysin CLECs which have been assessed as to their pH dependence and stability, stability at elevated temperature, resistance to exogenous proteolysis and stability in the presence of an organic solvent. Thermolysin CLECs were compared to soluble thermolysin, as described in detail in Examples 2 and 4 and FIGS. 1–4 and 6. Results of the assessment showed the following:

1. As to pH dependence and stability, both forms demonstrate maximum activity at pH 7 and demonstrate similar activity in the acidic range. In the alkaline pH range, the CLEC maintains maximum activity to pH 10; the soluble thermolysin has 75% activity at pH 8.5, only 25% activity at pH 9 and is completely inactive at pH 9.5.

2. The additional stabilization achieved in CLECs results in enzymatic activity at higher temperatures than is possible with soluble thermolysin. Enhanced stability of CLEC thermolysin at lower temperatures makes storage simpler than it is for the soluble enzyme. Thermal stability and resistance to autolysis was also demonstrated for thermolysin CLECs, which retained maximum activity after five days of incubation at 65° C. In contrast, soluble thermolysin lost 50% of its initial activity after two hours incubation and demonstrated negligible activity after 24 hours incubation at 65° C.

3. Enzymatic activity of thermolysin CLECs was unaffected by four days' incubation in the presence of the powerful streptococcal protease, Pronase®. In contrast, soluble thermolysin was rapidly degraded and lost all activity after 90 minutes incubation.

Figure 5A:
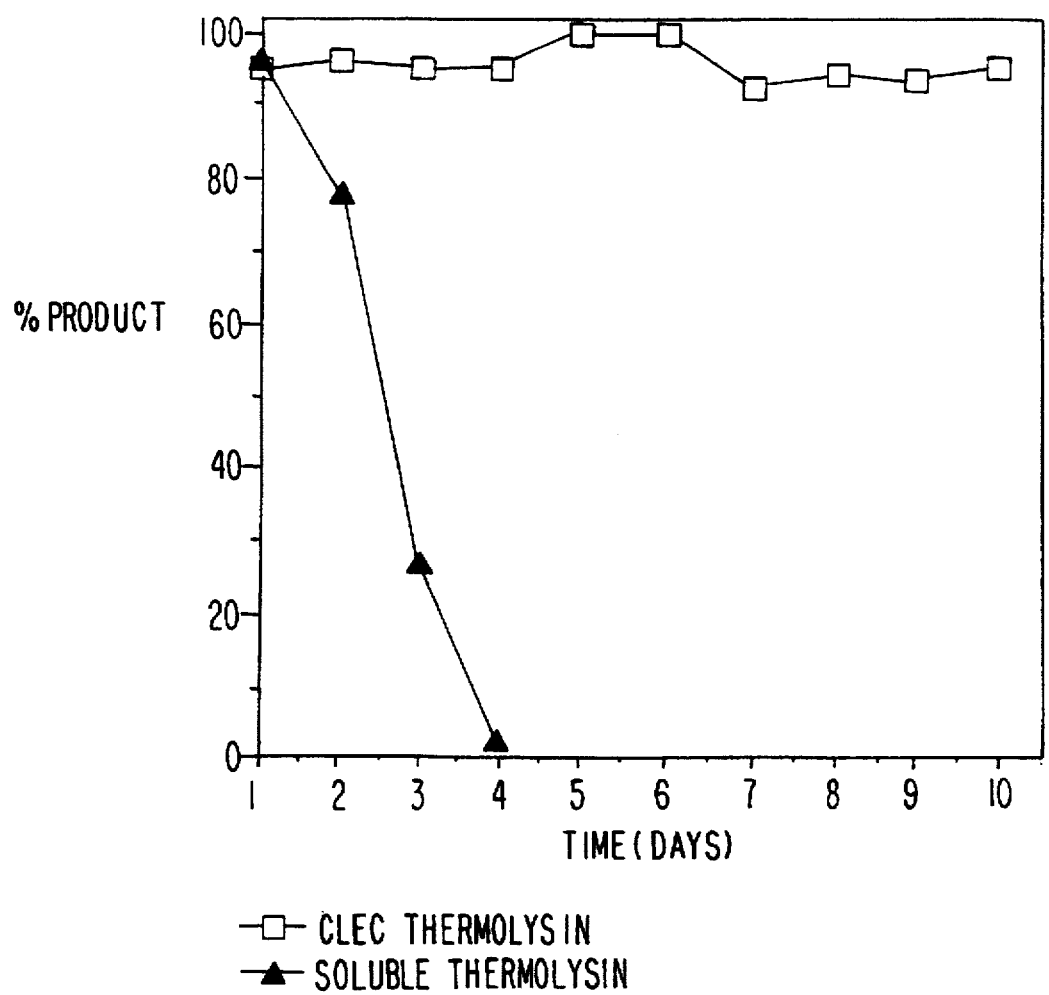
FIGS. 5A-5C are a series of graphic representations of results of assessment of continuous batch synthesis of the aspartame precursor using soluble thermolysin and CLEC thermolysin.
Figure 5B:
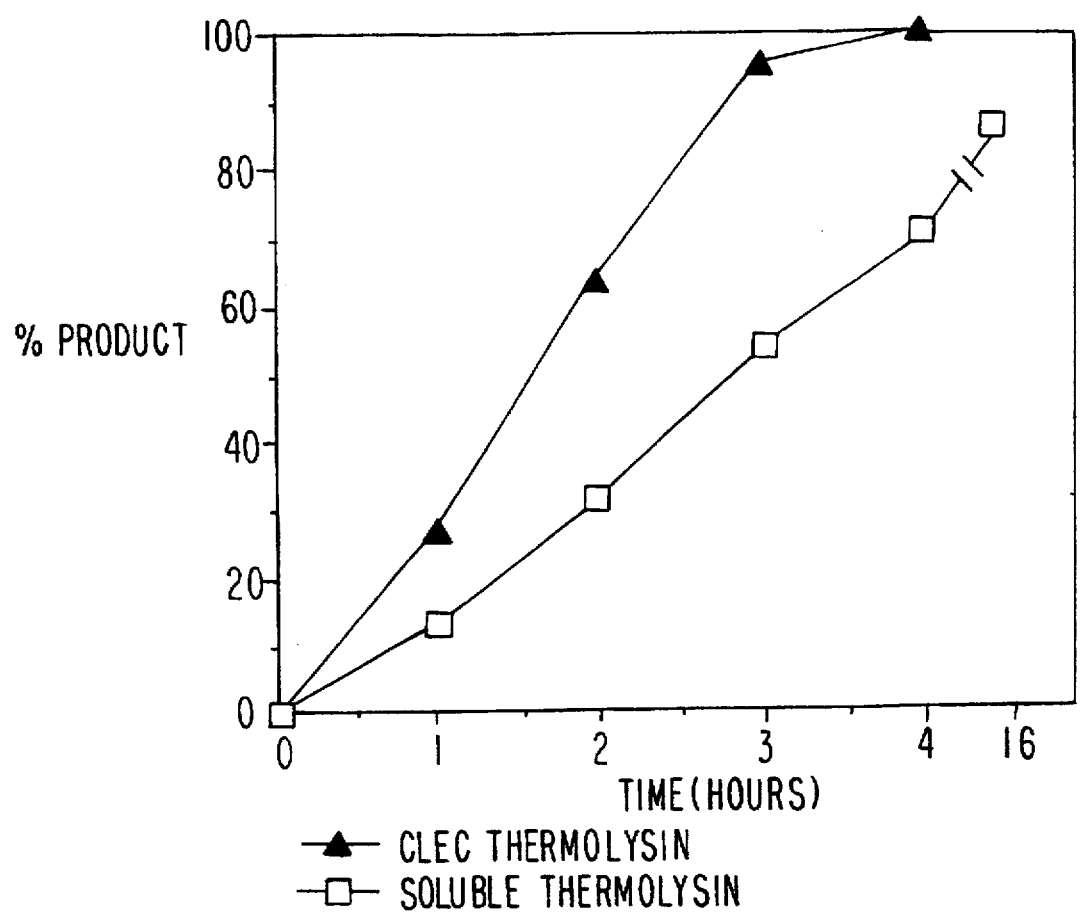
Figure 5C:
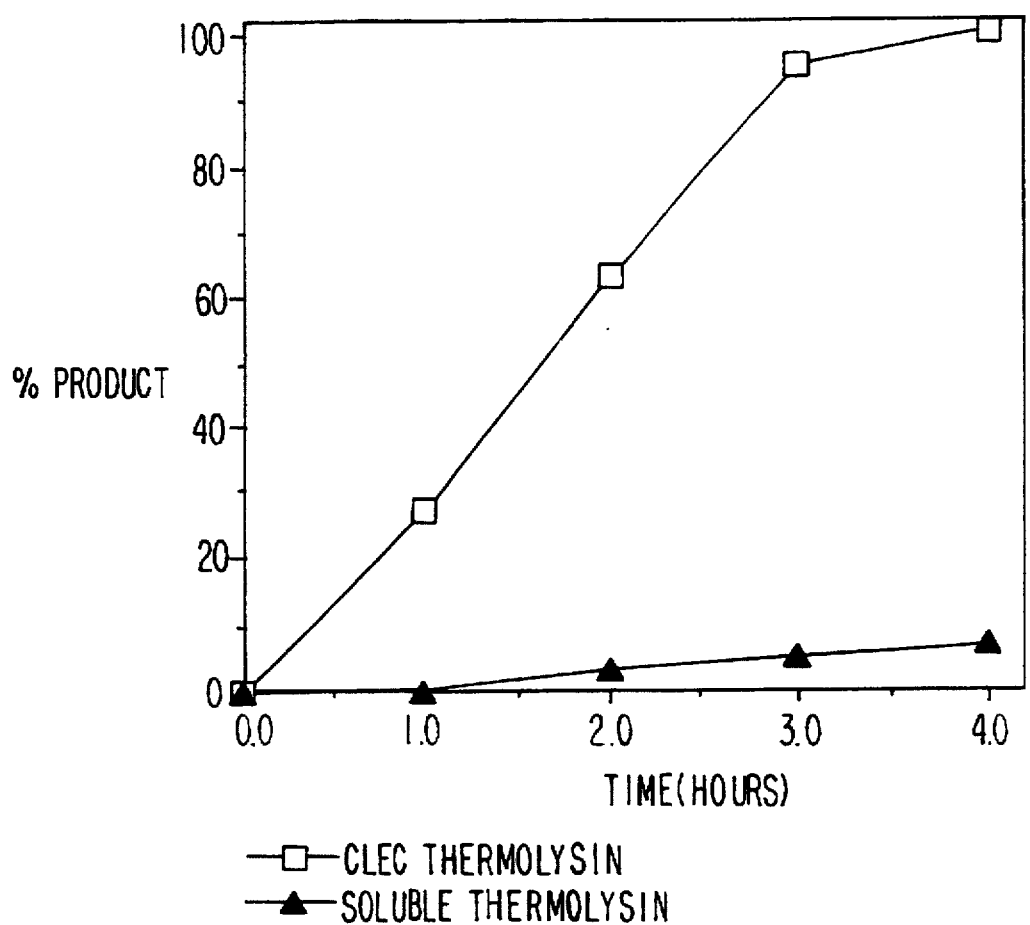

4. Thermolysin CLECs and soluble thermolysin exhibited markedly different stability in the presence of organic solvents, as shown in Table 7. The thermolysin CLECs retained greater than 95% maximum activity following incubation with all organic solvents assessed. Additional work with soluble and CLEC thermolysin catalysed synthesis is described in Example 2 and FIG. 5.

5. Thermolysin CLECs and free thermolysin had comparable initial enzymatic activity. Thermolysin CLECs retained their initial activity after 18 days of continuous batch synthesis of the aspartame precursor in organic solvent at high temperature. In contrast, free thermolysin rapidly lost its activity and by day four was inactive. This work is described in Example 4 and FIG. 6.

These features of thermolysin CLECs and other enzyme CLECs make them particularly useful, since they are easier to store, more stable and less easily inactivated or degraded than corresponding soluble enzymes.

Assessment of Lipase CLECs

Figure 7:
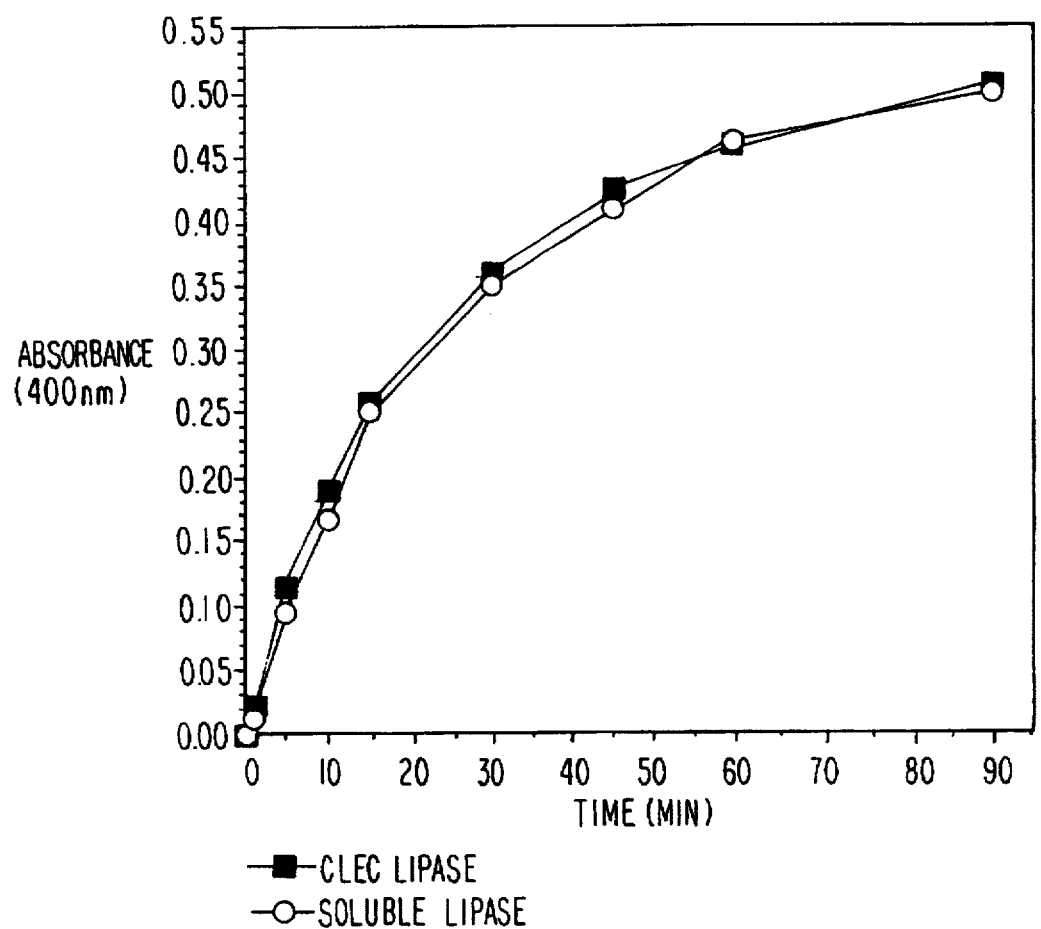
FIG. 7 is a graphic representation of results of the assessment of enzymatic activity for soluble lipase and the corresponding lipase CLEC.

The method of the present invention has also been used to produce lipase CLECs which have been assessed as to their activity. Lipase CLECs were compared to soluble lipase, as described in detail in Examples 5–8 and FIGS. 7 and 8. Results of the assessment demonstrated that *G. candidum* and *C. cylindracea* lipase CLECs retain significant activity, compared to soluble enzyme (Examples 5–7) and that the porcine pancreatic lipase retained activity to a lesser extent. (Example 8)

Applicability of CLECs

As disclosed here, CLECs represent a novel technology with broad use in many areas, including, but not limited to, industrial scale syntheses, laboratory tools, biosensors, and medical applications. Examples of various systems using conventionally immobilized enzyme methods in their execution are given in Tables 2–5 of the referenced commonly-owned patent applications. One skilled in the art should be able to adapt these, and similar systems, to the CLEC technology disclosed in this application.

For example, thermolysin CLECs are useful for producing the chiral precursor (Z-Asp-Phe-O-Me-H-Phe-OMe) of aspartame, as shown herein. In addition, lipase CLECs have a variety of uses, such as in the production of edible products (e.g., cocoa fat or other fat substitutes produced by acting upon an edible oil, such as palm oils); in the resolution of racemates by stereo-selective synthesis; in the production of herbicides (e.g., R(+)2 phenoxypropionic acids, by acting on 2 chloro propionic acids); and in the production of β blockers. These and other uses are also described in the referenced commonly-owned patent applications.

CLECs made by the present method can also be used for medical purposes, both therapeutic and diagnostic. As described herein, enzymes which have potential for such uses have been crystallized and crosslinked and assessed as to their enzymatic activity and stability under various conditions. For example, lipase CLECs have been produced and shown to retain significant enzymatic activity. Such lipase CLECs can be used, for example, to treat individuals with pancreatic insufficiency and/or fat malasorption conditions, in which lipase secretion is abnormally low. This can be associated with steatorrhea, essential fatty acid deficiency, loss of a high calorie source (fat) or a fat-soluble vitamin deficiency. Presently available approaches to lipase supplementation have numerous short-comings, which limit their effectiveness. For example, gastric acid inactivation of enzyme supplements or digestion by proteases of lipase-supplementation agents may occur, reducing the available amount of the agent(s) used. Possible supplementation strategies include high doses of pancreatic enzymes, use of pH sensitive enteric-coated microspheres and capsules, gastric acid modulation and use of acid resistant lipases (which presently are unavailable). Lipase CLECs can be used as therapeutic agents or drugs and, in this context, have several key advantages: they are stable to exogenous proteolysis, stable to pH levels which would inactivate or destroy other enzyme forms, stable to heat and solvents and easily stored because they can be lyophilized; as described herein.

In therapeutic applications, design and use of CLECs which release the enzyme over time (e.g., slow or controlled release) might prove advantageous, such as to provide the activity over time or to delay its release (e.g., to allow the enzyme to pass through harsh pH conditions in the stomach by being protected in CLEC form and then being released). Production of CLECs in which cross-linking and/or crystallization is designed to permit slow or controlled release would provide useful agents.

CLECs may also be used as laboratory reagents in small columns or in batch processes, which can be used to carry out laboratory reactions. For example, lipase CLECs can be used for stereoselective syntheses, including esterification, transesterification, aminolysis, polycondensations, acylation, oximolysis and resolution of racemic mixtures.

The advantages of CLEC catalyzed reactions for laboratory use are threefold. First, CLEC retain high activity in harsh environments (eg. aqueous, organic, near-anhydrous solvents and mixtures of these, and at high temperatures) that are typical of laboratory chemical synthesis experiments. Second, CLEC exhibit high operational and storage stability, which is appropriate for intermittent laboratory experiments. Third, their high activity per unit volume will allow shorter reaction times and require smaller volumes of thzyme (per unit of activity). Thus, the advantages that CLECs offer over free or immobilized enzymes, provide organic chemists with an alternative, highly selective, synthetic tool.

In all of these instances described above, but not limited to these, the method of this invention can be adapted by one of ordinary skill in the art, to convert a process using a conventionally immobilized enzyme catalyst to the use of a CLEC of the appropriate enzyme. CLECs can not only replace conventional immobilized enzymes, but also be used in cell mediated transformations.

The present invention will now be illustrated by the following Examples, which are not intended to be limiting in any way.

EXAMPLE 1
Crystallization and crosslinking of thermolysin for synthesis of the aspartame precursor, Z-Asp-Phe-OMe Crystallization 250 mg of thermolysin from *Bacillus thermoproteolyticus* was purchased from Boehringer-Mannheim GmbH, and dissolved in 4 ml of 45% dimethyl sulfoxide (DMSO) and 55% 1.40M calcium acetate, 0.50M sodium cacodylate at pH 6.5. These starting conditions are similar to those described by Matthews et. al. for the production of diffraction quality thermolysin crystals (see, eg., Holmes and Matthews, *J. Mol. Biol.* 160:623–639 (1982)). The protein solution was then concentrated to 1 ml in a Centricon 10 micro-concentrator. A good yield of microcrystals was obtained by a process of flash crystallization, now disclosed here, in which 1 ml of water, or 1.40M calcium acetate, 0.50M sodium cacodylate at pH 6.5, was rapidly injected into either of the thermolysin-DMSO solutions described above. A shower of hexagonal microcrystals of approximately uniform dimensions (approx. $10^{-1}$ mm in length) results from this process.

Crosslinking of thermolysin microcrystals

The protocol used in this specific example of the method of this invention is an adaptation of that described by Nakanishi et al. (*Biotechnology* 3:459–464 (1985)), in which protocol, thermolysin was first adsorbed onto a carrier bead composed of the ion-exchange resin Amberlite XAD-7, and subsequently immobilized by cross-linking with glutaraldehyde (Quiocho and Richards, *Proc. Natl. Acad. Sci. (USA)* 52:833–839 (1964)). In this exemplification, the microcrystals of thermolysin obtained above were centrifuged and pelleted, and the supernatant was discarded. 5 ml of 17.5% technical grade glutaraldehyde, in 2.5 % DMSO, 0.05M calcium acetate, and 0.025M sodium cacodylate at pH 6.5, were then added to the microcrystals. The mixture was incubated with gentle agitation at 37° C. for 4 hours. The crosslinking reaction was stopped by repeated washing of the crystals with 10 ml aliquots of water to remove the glutaraldehyde solution. The washed cross-linked thermolysin crystals constitute the thermolysin CLEC used below as a catalyst.

Synthesis of Z-Asp-Phe-OMe in an aqueous solution 5 ml of a thermolysin CLEC suspension were added to a continuous stirred-batch reactor incubated at 37° C. After centrifugation and decantation of the supernatant, an aqueous reaction mixture was added to the CLECs. This solution was prepared by mixing 80 mg of Z-L-Asp and 80 mg of L-Phe-OMe-HCl in 1 ml of water, with acetic acid added to obtain a pH of 7.0. Samples were taken for analysis by HPLC. Table 1 below shows the HPLC peak height of the Z-L-Asp substrate peak after the indicated time of reaction, normalized to 1 at time t=0. Since Z-L-Asp is rate limiting in this reaction, measuring its depletion is equivalent to measuring the appearance of product Z-L-Asp-L-Phe-OMe (Nakanishi et al. *Biotechnology* 3:459–464 (1985)). Table 1 also includes the normalized peak height of limiting Z-L-Asp substrate remaining, and an estimate of the degree of completion of the reaction. It is clear that the reaction proceeded to about 20% completion within the first 30 seconds and plateaued there. These results are consistent with the observations of Nakanishi et al. (*Biotechnology* 3:459–464 (1985)) when using conventionally immobilized thermolysin in an aqueous reaction mixture as above, and are attributable to the sparing solubility of the Z-L-Asp-L-Phe-OMe product in water.

TABLE 1

| Reaction Time (sec) | Peak Height (Normalized) | Percent Completion |
| --- | --- | --- |
| 0 | 1.000 | |
| 30 | 0.727 | 27.3% |
| 60 | 0.857 | 14.3% |
| 120 | 0.940 | 6.0% |
| 180 | 0.797 | 20.3% |

Synthesis of Z-Asp-Phe-OMe in a near-anhydrous solution 5 ml of a thermolysin CLEC suspension were added to a continuous stirred-batch reactor incubated at 37° C. After centrifugation and decantation of the supernatant, a near-anhydrous organic reaction mixture was added to the CLECs. This solution was prepared by mixing 80 mg of Z-L-Asp and 240 mg of L-Phe-OMe in 1 ml of 99% ethyl acetate and 1% water. Samples were taken for analysis by HPLC. Table 2 below shows the HPLC peak height of the Z-L-Asp substrate peak after the indicated time of reaction, normalized to 1 at time t=0. Since Z-L-Asp is rate limiting in this reaction, measuring its depletion is equivalent to measuring the appearance of product Z-L-Asp-L-Phe-OMe (Nakanishi et al. *Biotechnology* 3:459–464 (1985)). Table 2 also includes the normalized peak height of limiting Z-L-Asp substrate remaining, and an estimate of the degree of completion of the reaction. In this case, the reaction proceeded to about 70% completion within the first 30 seconds and plateaued there. These results are also consistent with the observations of Nakanishi et al. (*Biotechnology* 3:459–464 (1985)) with conventionally immobilized thermolysin in a near-anhydrous reaction mixture, and are attributable to product inhibition of the enzyme.

TABLE 2

| Reaction Time (sec) | Peak Height (Normalized) | Percent Completion |
|---|---|---|
| 0 | 1.000 | |
| 30 | 0.323 | 67.7% |
| 60 | 0.314 | 68.6% |
| 120 | 0.305 | 69.5% |
| 180 | 0.272 | 72.8% |

EXAMPLE 2
Crystallization, cross-linking and lyophilization of thermolysin and assessment of characteristics of resulting product
Crystallization of thermolysin Thermolysin (Diawa Kasei K.K., Japan) was dissolved in 10 mM calcium acetate (Sigma), pH 10.0, to a concentration of 10% (w/v). The pH of the solution was maintained at 10.0 by titration with 2M NaOH. Following complete solubilization, the protein solution was titrated to pH 8.0 with 2M HCl. Solid calcium acetate was added to 1.2M. Dimethyl sulfoxide (Sigma) was then added to 30%. The protein was concentrated to 100 mg/ml by ultrafiltration in an Amicon stir cell (10,000 MWCO membrane). Concentrated enzyme was aliquoted and stored at $-70°$ C. Thermolysin was crystallized by the addition of 9 volumes demineralized water to 1 volume concentrated (100 mg/ml) protein solution. The solution was briefly vortexed and allowed to stand overnight at room temperature. Crystals were washed with 10 volumes of 10 Mm calcium acetate pH 7.0 and recovered by low speed centrifugation (10 min at 1500×G, Beckman GPR centrifuge).

The rapid addition of water to a concentrated (100 mg/ml) solution of thermolysin induces the formation of crystals which become visible under low-power magnification within ten minutes. Crystal size is reproducibly dependent on the final protein concentration. Three volumes of water to one volume of thermolysin concentrate (100 mg/ml) will produce 0.5 mm long, X-ray diffraction quality hexagonal rods that correspond to the crystals described earlier by Colman et al. (Colman, P.M., et al. *J. Mol. Biol.* 70:701–724 (1972)), as confirmed by us by diffraction analysis. Adding ten volumes of water to one of protein concentrate reduces the length of the resulting crystals to 0.05 mm. These micro-crystals are preferred in CLEC applications, since they tend to minimize diffusion problems related to crystal size (see eg., Quiocho, F. A. and Richards, F. M. *Biochemistry* 5:4062–4076 (1967)). Within a given batch of protein, crystal size was consistently uniform. (Crystals 0.05–0.10 mm in length were used in this study to facilitate accurate pipetting of crystalline suspensions.) Densitometer scans of SDS-PAGE showed a six-fold purification of the enzyme on crystallization, significantly increasing the specific activity of the CLECs. Crystallization resulted in a 20% decrease in the total activity of the CLEC protein compared to soluble thermolysin, when assayed by spectrophotometric cleavage of the dipeptide substrate furylacryloyl-glycyl-L-leucine-amide (FAGLA), as described below.

Crosslinking of thermolysin crystals

Thermolysin crystals were crosslinked for 3 hours at room temperature in a solution of 12.5% glutaraldehyde (Sigma), 5% DMSO and 50 mM Tris pH 6.5. The crosslinked crystals were washed 3 times in demineralized water and recovered by low speed centrifugation, as described respect to crystallization of thermolysin. Chemical cross-linking of enzyme crystals stabilizes the crystal lattice and the constituent enzyme molecules in the crystal sufficiently so as to permit the practical use of CLECs in environments that are otherwise incompatible with enzyme function. There was no measurable difference in enzymatic activity between the crosslinked and uncrosslinked crystals when assayed (spectrophotometrically) by monitoring cleavage of the dipeptide substrate FAGLA (described below). Moreover, cross-linking stabilizes CLECs to the point that they can be lyophilized, with retention of full enzymatic activity upon reconstitution in aqueous, organic, and mixed aqueous-organic solvents as shown in FIG. 1 and Table 3. Although crystallization resulted in a 30% decrease in the specific activity of the CLEC protein compared to soluble thermolysin, crosslinking and lyophilization of the CLECs did not further diminish specific activity.

TABLE 3

Thermolysin Activity

| | | Absorbance 345 nm | |
|---|---|---|---|
| | Time (min) | CLEC | Soluble Enzyme |
| 1 | 0.0 | 0.314 | 0.315 |
| 2 | 1.0 | 0.272 | 0.271 |
| 3 | 3.0 | 0.235 | 0.218 |
| 4 | 5.0 | 0.204 | 0.198 |
| 5 | 10.0 | 0.184 | 0.185 |
| 6 | 15.0 | 0.183 | 0.184 |

Enzymatic activity of soluble and CLEC thermolysin

The catalytic activity of soluble and CLEC thermolysin was assayed (Feder, J. and Schuck, J. M., *Biochemistry* 9:2784–2791 (1970)) by hydrolysis of the blocked dipeptide substrate furylacryloyl-glycyl-L-leucine-amide (FAGLA) (Schweizerhall). Cleavage of the amide bond was measured spectrophotometrically by a decrease in absorbance at 345 nm. Initial enzyme concentration was $10^{-7}$M by Bradford protein determination and densitometer scanning (Pharmacia LKB UltroScan XL) of Coomassie stained SDS-PAGE gels. CLEC enzyme is defined as reconstituted lyophilized cross-linked thermolysin crystals. Soluble enzyme is defined as thermolysin concentrated to 100 mg/ml. Enzyme was added to a 5 ml reaction volume containing substrate. Aliquots of the reaction mix were removed at the indicated times, and absorbance at 345 nm was measured. CLEC thermolysin was separated from the reaction mix by brief centrifugation (Beckman, microcentrifuge E) before reading absorbance. Absorbance was fitted to a pseudo first order rate equation and kcat/Km was calculated by dividing the fitted value by enzyme concentration (Multifit 2.0 Curve Fitting for the Apple Macintosh Computer, Day Computing P.O. Box 327, Milton, Cambridge CB4 6WL, U.K. (1990)).

pH Dependence and Stability

Figure 2:
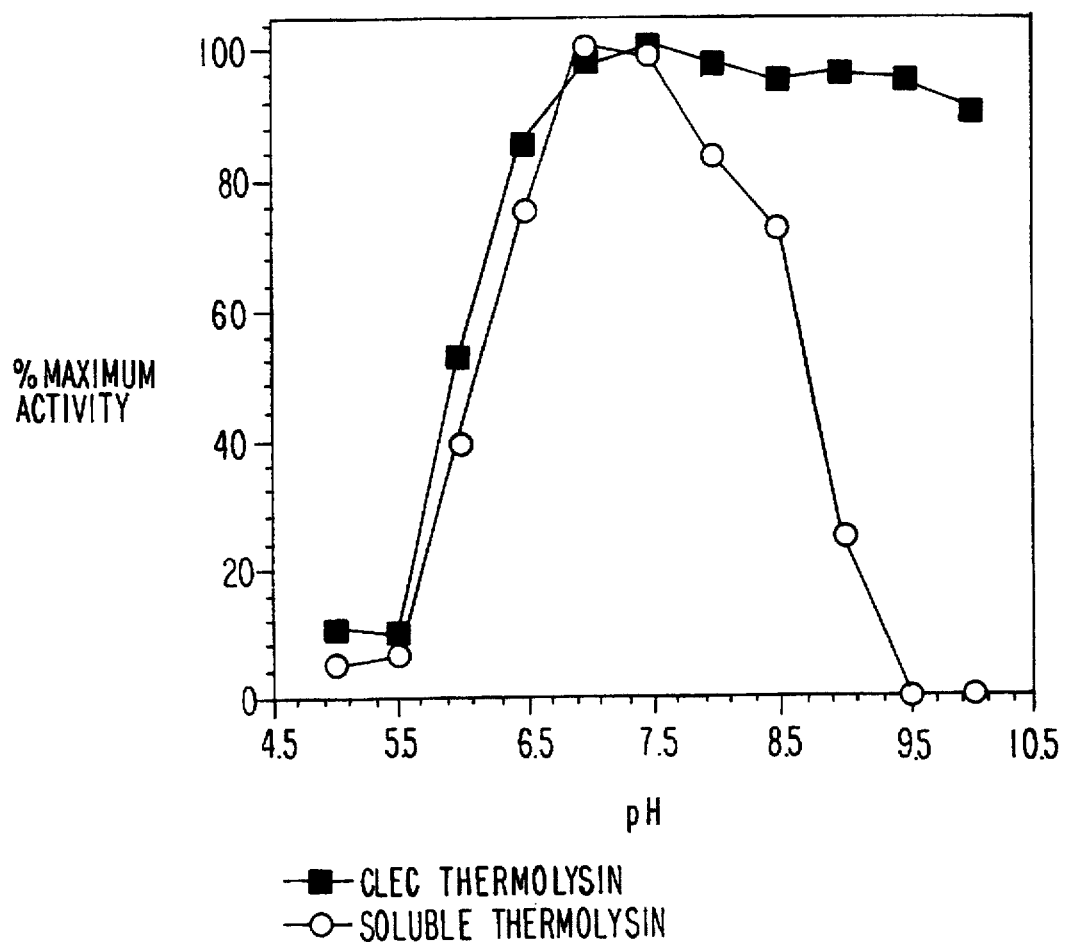
FIG. 2 is a graphic representation of results of a comparison of pH dependencies of thermolysin CLEC and soluble thermolysin.

The pH optimum and stability of the soluble enzyme were compared to that of thermolysin CLECs by cleavage of the dipeptide substrate FAGLA. Results are shown in FIG. 2 and Table 4. Both soluble and crystalline enzyme forms demonstrate maximum activity at pH 7. CLECs and soluble thermolysin also demonstrated similar activity in the acidic range and the bell shaped pH profile generated by the soluble enzyme was in good agreement with published data (Feder, J. and Schuck, J. M., *Biochemistry* 9:2784–2791 (1970)). In the alkaline pH range, however, the crystalline enzyme maintains maximum activity, to pH 10, while the soluble enzyme has 75% activity at pH 8.5, and only 25% activity at pH 9. At pH 9.5, the soluble enzyme is completely inactive.

TABLE 4

Thermolysin pH Curve

| pH | % Maximum Activity | |
|---|---|---|
|  | CLEC | Soluble Enzyme |
| 1 | 5.0 | 10.250 | 5.170 |
| 2 | 5.5 | 9.750 | 6.070 |
| 3 | 6.0 | 52.500 | 39.100 |
| 4 | 6.5 | 85.000 | 74.610 |
| 5 | 7.0 | 97.500 | 100.000 |
| 6 | 7.5 | 100.000 | 98.650 |
| 7 | 8.0 | 97.500 | 82.920 |
| 8 | 8.5 | 95.000 | 71.910 |
| 9 | 9.0 | 96.250 | 24.720 |
| 10 | 9.5 | 95.000 | 0.000 |
| 11 | 10.0 | 90.000 | 0.000 |

Stability at elevated temperature

One can achieve higher reaction rates and lower diffusion times for substrates and products by operating a given chemical process at higher temperature, where one is usually limited by the temperature stability of substrates and products. In enzyme-based catalysis, however, it is often the loss of enzymatic activity that sets the practical limit on the temperature at which a process can be run. The additional stabilization achieved in CLECs allows for enzymatic activity at much higher temperatures than is possible for soluble enzyme.

The enhanced stability at lower temperatures simplifies the routine long term storage of the CLEC catalysts. For example, it was necessary to store concentrated (>50 mg/ml) solutions of soluble thermolysin at −80° C. to retain maximum specific activity. At room temperature, activity was usually lost within one day. In contrast, rehydrated thermolysin CLECs could be routinely stored for months at room temperature with no apparent loss of activity. Unreconstituted lyophilized CLECs of thermolysin appear to be viable indefinitely.

Thermal stability and resistance to autolysis were demonstrated in thermolysin CLECs following incubation at 65° C. for five consecutive days (FIG. 3 and Table 5). Thermolysin CLECs retained maximum activity after five days incubation at elevated temperature. In contrast, the soluble thermolysin lost 50% of its initial activity after only two hours incubation and demonstrated negligible activity after 24 hours incubation at 65° C.

TABLE 5

Thermolysin Thermal Stability at 65° C.

| Time | % Maximum Activity | |
|---|---|---|
| (days) | CLEC | Soluble Enzyme |
| 0.000 | 100.000 | 100.000 |
| 0.041 |  | 70.000 |
| 0.083 | 96.000 | 50.000 |
| 0.164 |  | 32.000 |
| 0.246 |  | 17.000 |

TABLE 5-continued

Thermolysin Thermal Stability at 65° C.

| Time | % Maximum Activity | |
|---|---|---|
| (days) | CLEC | Soluble Enzyme |
| 0.410 | 97.0 | 10.000 |
| 1.000 | 101.0 | 2.000 |
| 2.000 | 97.0 |  |
| 3.000 | 94.0 |  |
| 4.000 | 96.0 |  |
| 5.000 | 92.0 |  |

The activity of soluble and CLEC thermolysin was measured following incubation at 65° C. Soluble thermolysin was incubated in 10 mM calcium acetate, 50 mM Tris pH 7.0 in a 65° C. water bath. The reaction volume was 500 µl. Final protein concentration was 10 mg/ml. Aliquots were removed at times 0, 1, 2, 4, 6, 10, and 18 hours. The samples were assayed by SDS-PAGE and FAGLA cleavage at room temperature as described above. For the thermolysin CLECs, a 250 µl crystal suspension in 10 mM calcium acetate and 50 mM Tris was also incubated in a 65° C. water bath. Activity was assayed at times 0, 1, 6, 24, 48, 72, 96, and 120 hours by FAGLA cleavage.

Resistance to exogenous Proteolysis

Assessment of the resistance of the thermolysin CLEC to the action of an exogenous protease was also carried out. SDS-PAGE (Sodium dodecyl sulfate poly acrylamide gel electrophoresis) analysis suggests that commercial enzymes can contain a substantial percentage of contaminants, some of which might have proteolytic activity against the principal soluble enzyme species. Given the packing of enzyme molecules in a crystal lattice one might assume that the interior enzyme molecules in a CLEC would be protected from proteolysis. To test this possibility, thermolysin CLECs and a soluble enzyme preparation were incubated in the presence of the streptococcal protease, Pronase®, a nonspecific protease capable of digesting most proteins to free amino acids (Calbiochem 1990 Catalog; LaJolla, Calif.).

Soluble and CLEC thermolysin were incubated in 50 mM Tris, pH 7.5, at 40° C. in the presence of the protease Pronase® (Calbiochem). The Pronase® to thermolysin ratio was 1/40. To inhibit thermolysin autolysis and prevent the proteolytic destruction of pronase by the thermolysin, EDTA was added to the soluble enzyme reaction to a final concentration of 100 mM (EDTA inhibits thermolysin activity but not Pronase®). At the times indicated aliquots were removed from the reaction mix and activity was assayed spectrophotometrically by cleavage of the dipeptide substrates FAGLA. To offset thermolysin inhibition due to the presence of EDTA, the spectrophotometric assay of soluble enzyme activity was performed in 0.5M calcium acetate buffer pH 7.0 and enzyme concentration was increased two fold. Crosslinked crystalline enzyme was assayed as described above.

As can be seen in FIG. 4 and Table 6, the soluble thermolysin was rapidly degraded and lost all activity after 90 minutes incubation. In contrast, the activity of the thermolysin CLEC was unaffected by four days incubation in the presence of protease. This near imperviousness to proteolysis is of particular interest in diagnostic biosensor applications where a suitable CLEC might be called upon to act in the presence of an unknown cocktail of naturally occurring proteolytic enzymes.

TABLE 6

| Time (days) | Protease Resistance % Maximum Activity | | Time (min) |
|---|---|---|---|
| | CLEC | Soluble Enzyme | |
| 1 | 0.000 | 100.0 | 100.0 | 0.000 |
| 2 | 0.003 | | 25.0 | 5.000 |
| 3 | 0.010 | | 17.5 | 15.000 |
| 4 | 0.021 | | 9.5 | 30.000 |
| 5 | 0.042 | 98.0 | 3.0 | 60.000 |
| 6 | 0.063 | | 1.0 | 90.000 |
| 7 | 0.084 | 101.0 | 0.0 | |
| 8 | 1.000 | 97.0 | | |
| 9 | 2.000 | 99.0 | | |
| 10 | 3.000 | 98.0 | | |
| 11 | 4.000 | 96.0 | | |

Stability in the presence of organic solvent

In order for enzymes to gain ideal acceptance as viable industrial catalysts, they must be able to function without excessive intervention in the practical environment of manufacturing processes. In particular, this would include the use of aqueous, polar and non-polar organic solvents, and mixtures of these. In commercial applications, aqueous-organic solvent mixtures allow manipulation of product formation by taking advantage of relative solubilities of products and substrates.

Soluble thermolysin and thermolysin CLECs exhibited markedly different stability in the presence of organic solvents. (Table 7) Soluble enzyme concentrations which could be incubated in organic solvent were limited to a maximum of 10 mg/ml. Concentrations greater than this value resulted in the instantaneous precipitation of thermolysin upon addition of organic solvent. In contrast, thermolysin CLEC concentrations were limited only by the volume occupied by the crystals. Soluble thermolysin retained the greatest activity (75%) following incubation in acetone, and the least (36%) in tetrahydrofuran. Following a one hour incubation in the presence of acetonitrile or dioxane the soluble enzyme lost approximately 50% of its initial activity. The CLEC thermolysin retained greater than 95% maximum activity following incubation with all organics assayed.

TABLE 7

| | Soluble Enzyme | % Maximum Activity CLEC |
|---|---|---|
| Acetonitrile | 42 | 102 |
| Dioxane | 66 | 97 |
| Acetone | 75 | 99 |
| THF* | 36 | 96 |

*Tetrahydro Puran

Stability in organic solvents

Thermolysin CLECs or soluble thermolysin preparations were incubated in 50% (v/v) solutions of the indicated organic solvents. A 100 μl slurry of thermolysin CLECs (10 mg/ml) in 10 mM Tris pH 7 was placed in a ½ dram glass vial. An equal volume of the indicated organic solvent was added and the mixture was briefly vortexed. Twenty μl of soluble thermolysin (100 mg/ml) was diluted in 80 μl of 0.015M Tris buffer pH 7.0 in a ½ dram glass vial. A 100 μl volume of organic solvent was then added to the protein solution and briefly vortexed. CLEC and soluble enzyme were incubated in the presence of organic solvent for one hour at 40° C. Following incubation, enzyme activity was assayed by cleavage of the dipeptide substrate FAGLA as described.

Low water concentration is thought to disfavor unfolding to intermediate states on the path to enzyme denaturation. In CLECs, this restriction of conformational mobility is provided by the inter-molecular contacts and cross-links between the constituent enzyme molecules making up the crystal lattice, rather than by the near-absence of water in the medium. As a result, intermediate water-organic solvent concentrations are readily tolerated by enzymes when formulated as CLECs, something previously unobserved with enzymes (see Table 7). This discovery opens up whole new areas of synthetic chemistry to exploitation using enzyme catalysis.

Even in near-anhydrous organic solvents, however, the routine use of enzymes has been hampered by their tendency to form ill-defined suspensions that are subject to clumping and other aggregation problems. This property makes these preparations inherently unattractive for large scale industrial processes. In contrast, CLECs and the constituent enzymes within the crystal lattice, remain mono-disperse in all these solvents.

Comparison with other immobilization methods

A number of useful reviews of enzyme immobilization methods have appeared in the literature (Maugh, T. H., Science 223:474–476 (1984)); Tramper, J., Trends in Biotechnology 3:45–50 (1985)). In these, the enzyme always represents a small fraction of the total volume of the immobilized particle, the bulk of it being inert carrier material. The carrier increases the mean free path between the solvent exterior of the immobilized enzyme particle and the enzyme active sites, exacerbating diffusion problems (Quiocho, F. A. and Richards, F. M., Biochemistry 5:4062–4076 (1967)).

In a CLEC, the crosslinked crystal matrix provides its own support, eliminating the need for a carrier. As a result, the concentration of enzyme in a CLEC is close to the theoretical packing limit that can be achieved for molecules of a given size, greatly exceeding densities achievable even in concentrated solutions. The entire CLEC consists of active enzyme, and thus, the diffusion-related reduction of enzyme reaction rates usually observed with conventionally immobilized enzymes relative to enzymes in solution are minimized (See FIG. 1), since the mean free path for substrate and product between active enzyme and free solvent will be greatly shortened for CLECs (compared to a conventional immobilized enzyme carrier particles). Importantly, the constituent enzyme in CLECs is intrinsically mono-disperse, and can be recovered by simple manipulations of the CLEC particles, such as filtration, centrifugation or decantation of solvent.

EXAMPLE 3

Soluble and CLEC Thermolysin-Catalysed Synthesis of the Aspartame Precursor Z-Asp-Phe-OMe Soluble and CLEC thermolysin catalysed synthesis of the aspartame precursor was performed in a repeated batch experiment. Three different experimental parameters were assessed: 1. thermolysin CLEC versus soluble thermolysin half-life, 2. thermolysin CLEC versus soluble thermolysin specific activity (equivalent protein concentration) and 3. thermolysin CLEC versus soluble thermolysin total activity (equivalent protein dry weight).

The reagents were prepared as follows:

Solvent—a buffer (50 mM MES-NaOH, 5 mM $CaCl_2$(2-[N-morpholino]ethane-sulfonic acid)(Sigma) saturated ethyl acetate, pH 6.0) saturated solution of ethyl acetate (Nakanishi, K. et al., Biotechnology 3:459–464 (1985)). The MES buffer was prepared by dissolving 9.76 g MES and 0.102 g $CaCl_2$ in 90 ml deionized water. The pH was adjusted to 6.0 with 5N NaOH. The volume was adjusted to 100 ml. To prepare buffer saturated ethyl acetate, 10 ml MES buffer was combined with 90 ml ethyl acetate in separatory funnel, following agitation the organic phase was collected.

Substrates—240 mM L-Phe-O-Me, 80 mM CBz-L-Aspartic Acid. L-Phe-O-Me was prepared by chloroform extraction of L-Phe-O-Me HCl. Equimolar amounts of L-Phe-O-Me HCl and $Na_2CO_3$ were dissolved in deionized water and agitated with an appropriate amount of chloroform to extract the L-Phe-O-Me. The chloroform was dehydrated with an appropriate amount of $MgSO_4$ and evaporated at 40° C. L-PheOMe was stored as a 2.4M solution in ethyl acetate at –20° C.

Thermolysin CLECS—0.216 mM thermolysin CLECs (7.5 mg/ml enzyme, approximately 15 mg/ml dry weight). Procedure for 3 ml batch reaction 0.214 g of N-CBz-L-Asp was dissolved in 9 ml buffer saturated ethyl acetate. 1 ml 2.4M Phe-O-Me stock as described above was added to the CBz-aspartic acid. Lyophilized CLECs or lyophilized soluble thermolysin was added to 3 ml of the reaction mix containing buffered solvent and substrates. The reaction was incubated at 55° C. with agitation, pH was maintained at 6.0. The CLECs remained insoluble and were removed from the reaction by filtration and low speed centrifugation. The conversion of substrates to product was monitored by removing 0.1 ml of reaction mix at 1 hr intervals for TLC or HPLC. The reaction volumes were scaled to 19 ml for the 24 hour continuous batch reactions. Assay of aspartame precursor product The progress of the reaction was followed by thin layer chromatography (TLC) (Lindeberg, G, *J. Chem. Education* 64:1062–1064 (1987)) (mobile phase; 1:1:3 water:acetic acid:N-butanol). Solid phase; silica gel. Visualize by UV at 245 nm and ninhydrin, and by high performance liquid chromatography (HPLC) (Nakanishi, K. et al. *Biotechnology* 3:459–464 (1985); Oyama, K. et al., *Meth. in Enzymology* 136:503–516 (1984), Ooshima, H. et al., *Biotechnology Letters* 7:789–792 (1985)). The reaction was monitored at 214 and 280 n. One hundred per cent conversion to product is defined as one hundred per cent conversion of CBz-aspartic acid to aspartame precursor. Continuous batch synthesis of the aspartame precursor (half-life)

Soluble and CLEC thermolysin catalysed synthesis of the aspartame precursor was performed continuously for 10 days in a repeated 24 hour batch experiment under the conditions described above. CLEC thermolysin concentration was 15 mg/ml dry weight. Soluble thermolysin (Diawa 10% protein) concentration was 37.5 mg/ml dry weight.

Product was recovered and fresh substrate was added to the reaction every 24 hr. Enzyme was recovered from the reaction mix by centrifugation and filtration. The % product was assayed by TLC and HPLC as described above (FIG. 5).

TABLE 8

Batch synthesis data (total activity)

| Time (hours) | CLECs | % Product Soluble |
|---|---|---|
| 0 | 0 | 0 |
| 1 | 27 | 0 |
| 2 | 63 | 3 |
| 3 | 95 | 5 |
| 4 | 100 | 7 |

EXAMPLE 4
Synthesis of the Aspartame Precursor (Z-Asp-Phe-OMe.H-Phe-OMe) by Thermolysin CLECs Thermolysin CLECs prepared as described herein were used to produce the chiral aspartame precursor N-(benzyloxycarbonyl)-L-aspartyl-L-phenylalanine methyl ester (Z-Asp-Phe-OMe-H-Phe-OMe). In this reaction, the thermolysin CLEC catalyzed a condensation reaction of the two substrates, CBz-L-Aspartic Acid and L-Phe-OMe. The reaction was carried out as a 24-hour continuous batch reaction and was terminated because of equipment failure. The reaction can be carried out for even longer periods of time and the subject data demonstrates essentially no loss of activity of the thermolysin CLEC in 18 days at 55° C. in buffer-saturated ethyl acetate.

Results of the reactions in which thermolysin CLECs or free thermolysin was used are included in Table 9 and shown graphically in FIG. 6. As can be seen, thermolysin CLECs and free thermolysin had comparable initial activity. As can also be seen, the thermolysin CLECs retained substantially all of their initial activity for the 18 days during which they were used; free thermolysin rapidly lost activity and by day four, was inactive.

TABLE 9

Enzymatic Activity of Thermolysin CLECs and Free Thermolysin Over an 18-Day Period (55° C., Buffer-saturated Ethyl Acetate)

| | % Starting Activity | |
|---|---|---|
| Time (Days) | Thermolysin CLEC | Free Thermolysin |
| 1.000 | 95.000 | 96.000 |
| 2.000 | 96.000 | 78.000 |
| 3.000 | 95.000 | 27.000 |
| 4.000 | 95.000 | 2.000 |
| 5.000 | 100.000 | |
| 6.000 | 100.000 | |
| 7.000 | 92.000 | |
| 8.000 | 94.000 | |
| 9.000 | 93.000 | |
| 10.000 | 95.000 | |
| 11.000 | 93.000 | |
| 12.000 | 93.000 | |
| 13.000 | 92.000 | |
| 14.000 | 90.000 | |
| 15.000 | 90.000 | |
| 16.000 | 91.000 | |
| 17.000 | 92.000 | |
| 18.000 | 90.000 | |

24 Hour Continuous Batch Reaction
Reaction Conditions
Volume—19 ml
Temperature—55° C.
Time—24 hr
Vessel—50 ml round bottom flask with teflon stopper and magnetic stir bar
Solvent—Buffer saturated ethyl acetate
Reagents
Solvent—Buffer saturated ethyl acetate (Nakanishi, K. et al., *Biotechnology* 3:459–464 (1985)). To prepare MES $CaCl_2$ buffer, dissolve 0.76 g MES and 0.102 g $CaCl_2$ in 90 ml deionized water. Adjust the pH to 6.9 with 5N NaOH. Adjust the volume to 100 ml. To prepare buffer saturated ethyl acetate, combine 10 ml buffer with 90 ml ethyl acetate in a separatory funnel, agitate, and collect the organic phase. Prepare fresh solvent daily.

Substrates 240 mM (4.3 mg/ml) L-Phe-O-Me; 80 mM (2.14 mg/mil) CBz-L-Aspartic Acid. L-Phe-O-Me is prepared by chloroform extraction of L-Phe-O-Me.HCl. L-Phe-O-Me.HCl is partitioned between chloroform and aqueous Na$_2$CO$_3$ (one equivalent). The chloroform layer is dried with anhydrous MgSO$_4$ and evaporated at 40° C. L-Phe-O-Me is stored as a 2.4M (43 mg/ml) solution in ethyl acetate at −20° C. CBz-L-Aspartic Acid is used as supplied by the manufacturer.

Enzyme—Thermolysin CLECs or free thermolysin. Final enzyme concentration for the 24 hour batch reaction equals 3.4×10$^{-5}$M, 1.2 mg/ml enzyme (approximately 2.4 mg/ml dry weight thermolysin CLECs).

Procedure

To prepare the reaction mix, dissolve 0.452 g N-CBz-L-Asp in 19 ml buffer saturated ethyl acetate and add 2.1 ml 2.4M Phe-O-Me stock. While stirring the reaction mix, add 45 mg of lyophilized thermolysin CLECs or an equivalent amount of lyophilized free thermolysin to yield an enzyme concentration of 3.4×10$^{-5}$ (1.2 mg/ml thermolysin). Incubate the reaction in a heating bath at 55° C. for 24 hours. At the end of each 24 hour batch reaction, the enzyme is recovered and the reaction cycle is repeated with fresh substrate. CLECs remain insoluble and are separated from the product and recovered for reuse by low speed centrifugation. The lyophilized free thermolysin forms an unevenly dispersed suspension in ethyl acetate and is removed from the reaction mix by centrifugation and filtration. Under these reaction conditions, thermolysin CLECs convert substrate to approximately 95% product in 24 hours at 55° C. Conversion of substrate to product is assayed by TLC or HPLC.

Product Assay

The progress of the reaction can be followed by thin layer chromatography (TLC) (Lindeberg, G., *J. Chem. Ed.* 64:1062–1064 (1987)) or by high performance liquid chromatograph (HPLC) (Nakanishi, K. et al., *Biotechnology* 3:459–464 (1985); Oyama, K. et al., *Eur. J. Biochem.* 161:541–549(1986)).

EXAMPLE 5

Crystallization, cross-linking and lyophilization of *Geotrichum candidum* lipase and assessment of characteristics of the resulting product Crystallization of lipase As disclosed here, the enzyme lipase (*Geotrichum(G.) candidum*) was crystallized by vapor diffusion from an aqueous solution of 20 mg/ml protein in 50 mM Tris pH 7 containing 8% ammonium sulfate. Bipyrimidal crystals were visible after 20 to 30 days incubation at room temperature. Crystals were recovered by centrifugation, as previously described in Example 2.

Cross-linking of lipase crystals

As disclosed here, lipase crystals were added to a solution of 12.5% glutaraldehyde and 50 mM Tris pH 5.6. The crystals were crosslinked for one hour. Following cross-linking the crystals were washed with three 15 ml volumes of 50 mM Tris pH 7.0. The lipase CLEC was lyophilized, as previously described in Example 2.

Enzymatic activity of soluble and CLEC lipase

The catalytic activity of soluble and CLEC lipase was assayed spectrophotometrically by monitoring hydrolysis of the substrate p-nitrophenyl acetate (Table 17 and FIG. 10). Cleavage was monitored by increasing absorbance at 400 nm. Initial substrate concentration was 0.005%. Enzyme concentration was 1.5×10$^{-8}$M. CLEC or soluble enzyme was added to a 5 ml reaction volume containing substrate in 0.2M Tris pH 7.0 at room temperature. As described previously in Example 2, CLEC enzyme was removed from the reaction mix by centrifugation prior to measuring absorbance.

TABLE 10

Lipase Activity

| | | Absorbance 400 nm | |
|---|---|---|---|
| | Time (min) | CLEC | Soluble Enzyme |
| 1 | 0.0 | 0.000 | 0.000 |
| 2 | 1.0 | 0.013 | 0.021 |
| 3 | 5.0 | 0.094 | 0.116 |
| 4 | 10.0 | 0.164 | 0.186 |
| 5 | 15.0 | 0.248 | 0.258 |
| 6 | 30.0 | 0.346 | 0.357 |
| 7 | 45.0 | 0.407 | 0.420 |
| 8 | 60.0 | 0.461 | 0.459 |
| 9 | 90.0 | 0.497 | 0.502 |

EXAMPLE 6

Crystallization and crosslinking of *Candida cylindracea* lipase and assessment of characteristics of the resulting product Crystallization of lipase Lyophilized *Candida cylindracea* lipase (9.98 mg dry weight) (Boehringer Mannheim) was dissolved in 0.5 ml of deionized water. Final protein concentration was 6 mg/ml. To induce crystallization, the lipase was dialysed against a low salt buffer. Five buffer conditions produced crystals suitable for CLEC formulation: Condition 1, Dialysis against 5 mM sodium phosphate buffer pH 6; Condition 2, Dialysis against 5 mM sodium phosphate buffer pH 7; Condition 3, Dialysis against 5 mM sodium phosphate pH 8; Condition 4, Dialysis against 20 mM Tris HCl pH 6.8; Condition 5, Dialysis against 20 mM Tris HCl pH 6.8 containing 1 mM CaCl$_2$ and 1 mM MgCl$_2$. All dialysis conditions produced a showering of lipase crystals; thin square plates 0.1 mm–0.05 mm in size. Crystallization was completed in six hours. Crystals were recovered by centrifugation as previously described. Lipase crystals were washed ten times with 20 mM buffer pH 6.8. Following washing, crystals were again recovered by centrifugation.

Cross-linking of Candida cylindracea lipase crystals

As disclosed here, lipase crystals were cross-linked in a solution of 7.5% glutaraldehyde and 20 mM Tris HCl pH 6.8 for 30 minutes at room temperature. Following cross-linking the crystals were washed exhaustively with 20 mM Tris HCl pH 6.8.

Enzymatic activity of CLEC lipase The catalytic activity of the lipase CLECs was assayed qualitatively by hydrolysis of the calorimetric substrate p-nitrophenyl acetate (Fluka) (M. Semeriva et al. *Biochem. Biophys. Res. Comm.* 58:808–813 (1974)). The presence of catalytic activity is indicated by the appearance of a yellow color in the assay solution. Several lipase CLECs were placed in a 100 μl solution of 3.12 mM p-nitrophenyl acetate containing 4% acetonitrile in 80 mM Tris HCl pH 7.5 at room temperature. To monitor spontaneous hydrolysis of the substrate, a negative control containing assay mix and buffer was prepared simultaneously. Soluble lipase was used as a positive control. Lipase CLECs were found to retain significant activity.

EXAMPLE 7

Crystallization and Crosslinking of *Candida Cylindracea* (CC) Lipase and Lyophilization of the Resulting CLECs Crystallization, crosslinking and lyophilization

*Candida cylindracea* lipase was purified to greater than 95% homogeneity (SDS-PAGE) from crude lyophilized protein (Meito Sangyo Co., Ltd., Tokyo). Purified CC lipase was crystallized by the dropwise addition of 50% (w/v) polyethylene glycol 8000 (PEG 8000) (Kodak) to a stirred 12–16 mg/ml lipase solution in 100 mM sodium acetate pH 6.5 buffer. Final precipitant concentration was 16–18%. Rod-shaped CC lipase crystals 10–50μ in length appeared within 30 minutes and crystallization was completed in 6–8 hours. Crystals were recovered by low speed centrifugation. The supernatant containing uncrystallized lipase was retained and the soluble lipase was recovered for subsequent crystallization. The crystals were washed with buffered 20% PEG.

The rod-shaped CC lipase crystals were cross-linked for 10 minutes at room temperature in a stirred solution of buffered 3% glutaraldehyde and 20% PEG 8000. Following initial cross-linking, ammonium sulfate was added to the cross-linking solution to a final concentration of 50 mM and the cross-linking reaction was continued for an additional 15 minutes. Following cross-linking, the crystals were washed once with buffered 50 mM ammonium sulfate, followed by exhaustive washing with sodium acetate buffer. CC lipase CLECs were lyophilized in 1 mM sodium acetate buffer pH 6.5, as described (Cooper, T. G., *The Tools of Biochemistry*; John Wiley and Sons, New York (1977), pp.379–380), and are stored in that form at room temperature without apparent deterioration.

Figure 8:
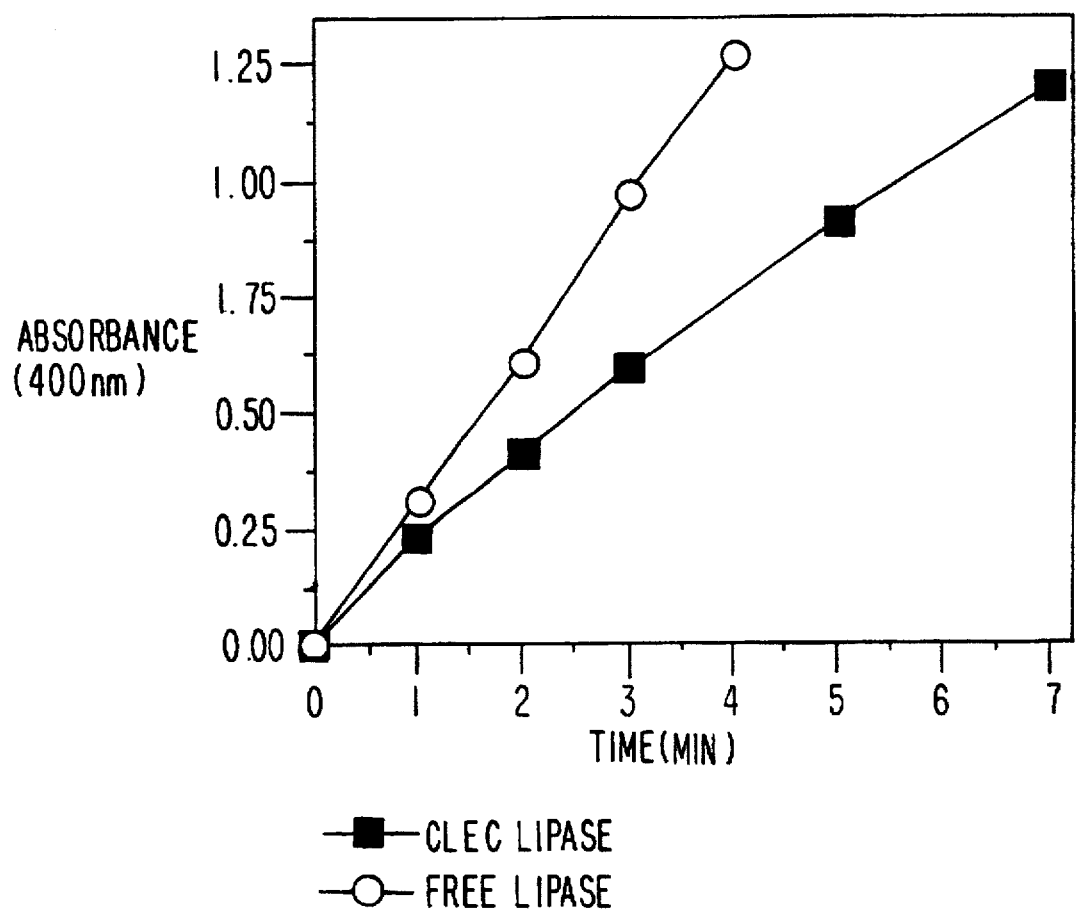
FIG. 8 is a graphic representation of the activity of *Candida cylindracea* lipase CLECs and of free *Candida cylindracea* lipase.

The rod-shaped CC lipase CLECs were found to be catalytically active, retaining 50% to 75% of the activity of the free enzyme, as shown in FIG. 8. Furthermore, CC lipase CLECs could be washed indefinitely in buffer, and even in deionized water, without deterioration or loss of activity; under these conditions, uncrosslinked crystals would quickly shatter and dissolve. The catalytic activity of CC lipase CLECs and of the free enzyme was assayed by hydrolysis of the calorimetric substrate p-nitrophenyl acetate (PNPA)(Fluka), as described (Semeriva, M. et al., *Biochem. Biophys. Res. Comm.* 58:808–813). Lipase catalyzed hydrolysis of PNPA was followed kinetically at room temperature and pH 7.5 in 50 mM sodium acetate buffer 4% acetonitrile by spectrophotometry (400 nm). CC lipase CLECs.

The crystallization conditions leading to the rodshaped CC lipase CLECs above were only one of many discovered in the course of the work described. A second set of conditions have been brought forward; the resultant CLECs have not been fully characterized as of yet. In this embodiment, lyophilized CC lipase (Boehringer Mannheim) was dissolved in 0.5 ml of deionized water to a final protein concentration of 6 mg/ml. Crystals were grown by microdialysis against various low salt buffer systems, including 5 mM phosphate at pH 6–8, 20 mM Tris HCl pH 6.8, and 20 mM Tris HCl pH 6.8, containing 1 mM $CaCl_2$ and 1 mM $MgCl_2$. All dialysis conditions produced showers of lipase crystals—thin square plates 0.1 mm–0.05 mm in size. Crystallization was completed in six hours. Crystals were recovered by centrifugation, and were washed ten times with 20 mM buffer pH 6.8. CC lipase crystals were cross-linked in a solution of 7.5% glutaraldehyde, 20 mM Tris HCl, pH 6.8 for 30 minutes at room temperature. Following cross-linking the crystals were washed exhaustively with 20 mM Tris HCl pH 6.8. These CLECs can be lyophilized as described above.

Assessment of Catalytic Activity of Linase CLECs

The catalytic activity of the lipase CLECs was assayed qualitatively by hydrolysis of the colorimetric substrate p-nitrophenyl acetate, as described above. These plate-shaped CC lipase CLECs were found to retain significant activity when compared to free enzyme; additional assessment is needed to determine if they are superior to the rod-shaped CC lipase CLECs

EXAMPLE 8

Porcine pancreatic lipase Purification.

The purification was based in large part on the published procedure of Roberts et al., *Lipids* 20:42–45 (1985). The following are the differences between the purification procedure used herein and the published protocol.

1. The initial extraction buffer, "buffer A" in the publication, does not contain sodium azide.
2. The procedure was followed exactly as published up through the butanol extraction and then the following additional steps were taken.
   A. The "creamy interface" resultant from the butanol extraction was resuspended in 150 ml publication "buffer B".
   B. The butanol extraction was repeated as described in the publication.

Two butanol extractions were performed instead of one.
3. The published procedure was followed up through the overnight dialysis and centrifugation. No column chromatography was run.
4. This procedure is run at 4× the published scale.
5. The final product is frozen at −20° C. Original crystallization
1. The frozen lipase was thawed and dialyzed vs. 5 mM cacodylate pH 7.0, 3.3 mM CaCl. Dialysate was centrifuged at 5000×G for 5 minutes. Supernatant was sequentially concentrated and diluted with 5 mM cacodylate pH 7.0 until the following conditions were reached:

Protein concentration=97 mg/ml $CaCl_2$ concentration=0.2 mM

Na taurodeoxycholate concentration=0.5 mM
2. Vapor diffusion.

Reservoir: 1.0 ml 10% (v/v) PEG 400 in $H_2O$

Drop: 5 ul protein from step #1+5 ul reservoir

A large number of rods were observed overnight under these conditions. Batch crystallization
1. Purified lipase was allowed to sit undisturbed in the cold room under the following conditions:

Protein concentration=46 mg/ml

Buffer=5 mM cacodylate pH 7.0, 0.02 mm $CaCl_2$, 0.5 mM Na taurodeoxycholate

Lipase sat from Dec. 6, 1991 to Jan. 7, 1992, when a large number of rod shaped crystals were observed.
2. These crystals were washed in 20% (v/v) PEG 400 and crushed. The following seeding was performed:

100 ul purified lipase in 5 mM cacodylate, pH 7.0 concentration=77 mg/ml 5 ul PEG 400

5 ul seeds

The lipase rods were observed to "crash out" almost instantly at room temperature. Cross-linking (original conditions)

Wash crystals in 30% PEG 400, 5 mM cacodylate, pH 7.0

Crosslink at room temperature in 3.3% glutaraldehyde for 1.5 hour

Wash in 20 mM Tris pH 8.0.

Specifically, the work with porcine pancreatic lipase was carried out as follows: PP lipase was purified to greater than 95% homogeneity (as determined by SDS-PAGE analysis) from a number of crude protein sources (sigma, Fluka, Boehringer-Mannheim and others). The purification was essentially as described (Roberts, J. et al., *Lipids* 20:42–45 (1985)), and is based on a combination of ammonium sulfate precipitation and multiple extractions using butanol-ammonium sulfate mixtures, but eliminating a gel filtration step in our case. This PP lipase material was dialyzed against 5mM cacodylate, pH 7, and was concentrated by ultrafiltration to about 100 mg/ml, 0.2 mM calcium chloride, 0.5 mM sodium taurodeoxycholate, pH 7. Crystals were initially obtained by vapor diffusion at 4° C., vs. a reservoir solution of 10% PEG 400. Sample droplets in this experiment consisted of 5 microliters of protein solution mixed well with 5 microliters of reservoir solution. The initial crystals were harvested and washed in 20% PEG 400, and crushed thoroughly for use as seeds in a batch crystallization. For that experiment, 5 microliters of 100% PEG 400, plus 5 microliters of our suspension of seeds in 20% PEG 400 were added to 100 microliters of an 80 mg/ml PP lipase solution in 5 mM cacodylate, pH 7, at room temperature. These conditions led to rapid showering of rod-shaped PP lipase crystals suitable for cross-linking. Crystals were washed extensively in 30% PEG 400, 5 mM cacodylate, pH 7 prior to crosslinking in 3.3% glutaraldehyde for 1½ hours. Crosslinked enzyme crystals were subsequently washed in 20 mM Tris, pH 8, a condition that would dissolve non-CLEC PP lipase crystals. These CLECs await further evaluation and optimization.

Equivalents

Those skilled in the art will recognize or be able to ascertain, using no more than routine experimentation, many equivalents to the specific materials and components described herein. Such equivalents are intended to be encompassed in the scope of the following claims.

We claim:

1. A thermolysin-catalyzed method of making a selected product, comprising the steps of:
   (a) combining at least one substrate and thermolysin, said thermolysin being in the form of a thermolysin crystal crosslinked with a multifunctional crosslinking agent, said crosslinked thermolysin crystal having resistance to exogenous proteolysis, such that said crosslinked thermolysin crystal retains at least 96% of its initial activity after incubation for 4 days in the presence of a concentration of Pronase™ that causes the soluble uncrosslinked form of the thermolysin that is crystallized to form said thermolysin crystal that is crosslinked to lose at least 99% of its initial activity after incubation for 90 minutes under the same conditions; and
   (b) maintaining the combination produced in step (a) under conditions which permit the thermolysin to act upon the substrate, thereby producing the selected product.

2. The method according to claim 1, wherein the product is a chiral organic molecule.

3. The method according to claim 1, wherein the product is a peptide.

4. The method according to claim 1, wherein the conditons in step (b) include a temperature of about 55° C.

5. The method according to claim 1, wherein the step (a), the combination further comprises a solvent selected from the group consisting of organic solvents, aqueous solvents and mixed aqueous/organic solvents.

6. The method according to claim 1, wherein in step (a), prior to being combined with the crosslinked thermolysin crystal, the substrate is combined with a solvent selected from the group consisting of organic solvents, aqueous solvents and mixed aqueous/organic solvents.

7. The method according to claim 1, wherein in step (b), the combination of the substrate and the crosslinked thermolysin crystal is maintained in a solvent selected from the group consisting of organic solvents, aqueous solvents and mixed aqueous/organic solvents.

8. The method according to any one of claims 5, 6 or 7, wherein the solvent is a mixed aqueous/organic solvent.

9. The method according to claim 1, wherein the thermolysin:Pronase™ ratio is 1:40.

10. The method according to claim 1, wherein the crystal is a microcrystal.

11. The method according to claim 10, wherein the microcrystal has a cross-section of $10^{-1}$ mm or less.

12. The method according to any one of claims 1, 5, 6 or 7, wherein the selected product is N-(benzyloxycarbonyl)-L-aspartyl-L-phynylalanine methyl ester, and the conditons of step (b) include a temperature greater than 45° C.

13. The method according to any one of claims 5, 6 or 7, wherein the solvent is a mixed aqueous/organic solvent.

14. The method according to claim 13, wherein the solvent is a water-ethyl acetate mixture.

15. The method according to claim 14, wherein the water-ethyl acetate mixture is buffer-saturated ethyl acetate and the conditions of step (b) include a temperature of approximately 55° C.

16. The method according to any one of claims 1, 5, 6 or 7, wherein the selected product is N-(benzyloxycarbonyl)-L-aspartyl-L-phenylalanine methyl ester and the substrates are N-(benzyloxycarbonyl)-L-aspartic acid and L-phenylalanine methyl ester.

17. The method according to any one of claims 5, 6 or 7, wherein the selected product is N-(benzyloxycarbonyl)-L-aspartyl-L-phenylalanine methyl ester, the substrates are N-(benzyloxycarbonyl)-L-aspartic acid and L-phenylalanine methyl ester and the solvent is a mixed aqueous/organic solvent.

18. The method according to claim 17, wherein the mixed aqueous-organic solvent is buffer-saturated ethyl acetate and the conditions in step (b) include a temperature greater than 45° C.

19. The method according to claim 18, wherein the temperature is approximately 55° C.

20. A method for producing aspartame comprising the steps of:
   (a) combining two peptides and thermolysin crystals, said crystals being crosslinked with a multifunctional crosslinking agent and having resistance to exogenous proteolysis, such that said crosslinked thermolysin crystals retain at least 96% of their initial activity after incubation for four days in the presence of a concentration of Pronase™ that causes the soluble uncrosslinked form of the thermolysin that is crystallized to form said crosslinked thermolysin crystals to lose at least 99% of its initial activity after incubation for 90 minutes under the same conditions, said first peptide having the formula L-Pne-OMe;
   (b) maintaining the resulting combination under conditions which permit condensation of the two peptides through action of the crosslinked thermolysin crystals, thereby producing a partially protected dipeptide of the formula Z-L-Asp-L-Phe-OMe, wherein Z represents a benzyloxycarbonyl group; and
   (c) removing the benzyloxycarbonyl group, thereby producing aspartame.

21. The method according to claim 20, wherein the conditions in step (b) include a temperature of approximately 55° C.

22. The method according to claim 20, wherein in step (a), the combination of the peptides and the crosslinked thermolysin crystals further comprises a solvent selected from the group consisting of organic solvents, aqueous solvents and mixed aqueous/organic solvents.

23. The method according to claim 20, wherein in step (a), prior to being combined with the crosslinked thermolysin crystals, the peptides are combined with a solvent selected from the group consisting of organic solvents, aqueous solvents and mixed aqueous/organic solvents.

24. The method according to claim 20, wherein in step (b), the combination of the peptides and the crosslinked thermolysin crystals is maintained in a solvent selected from the group consisting of organic solvents, aqueous solvents and mixed aqueous/organic solvents.

25. The method according to any one of claims 22, 23 or 24, wherein the solvent is a mixed aqueous/organic solvent.

* * * * *